United States Patent
Claypool et al.

(10) Patent No.: US 9,492,290 B2
(45) Date of Patent: Nov. 15, 2016

(54) TIBIAL PROSTHESIS SYSTEMS, KITS, AND METHODS

(71) Applicants: Zimmer, Inc., Warsaw, IN (US); Synvasive Technology, Inc., El Dorado Hills, CA (US)

(72) Inventors: Jody Claypool, Columbia City, IN (US); Wayne Paprosky, Winfield, IL (US); David Lewallen, Rochester, MN (US); Steven Stump, Goshen, IN (US); Barjinder S. Chana, Rancho Cordova, CA (US); Michael G. Fisher, Folsom, CA (US); Kenneth D Johannaber, Rancho Murieta, CA (US); Andrew P. Sizelove, Folsom, CA (US); Stephen E. White, Fort Wayne, IN (US)

(73) Assignees: Zimmer, Inc., Warsaw, IN (US); Synvasive Technology, Inc., El Dorado Hills, CA (US)

( * ) Notice: Subject to any disclaimer, the term of this patent is extended or adjusted under 35 U.S.C. 154(b) by 711 days.

(21) Appl. No.: 13/837,294

(22) Filed: Mar. 15, 2013

(65) Prior Publication Data

US 2013/0261504 A1 Oct. 3, 2013

Related U.S. Application Data

(60) Provisional application No. 61/618,376, filed on Mar. 30, 2012, provisional application No. 61/740,268, filed on Dec. 20, 2012.

(51) Int. Cl.
*A61F 2/38* (2006.01)
*A61F 2/46* (2006.01)
(Continued)

(52) U.S. Cl.
CPC ........... *A61F 2/4684* (2013.01); *A61B 5/1036* (2013.01); *A61F 2/389* (2013.01);
(Continued)

(58) Field of Classification Search
CPC ............... A61F 2005/0188; A61F 2002/2892; A61F 2/3868
USPC ................................ 623/20.14, 20.32–20.34
See application file for complete search history.

(56) References Cited

U.S. PATENT DOCUMENTS

| 4,501,266 A | 2/1985 | McDaniel |
| 4,944,757 A | 7/1990 | Martinez et al. |

(Continued)

FOREIGN PATENT DOCUMENTS

| AU | 2011343440 B2 | 4/2014 |
| CN | 1174498 A | 2/1998 |

(Continued)

OTHER PUBLICATIONS

"U.S. Appl. No. 13/836,665, Examiner Interview Summary mailed Jul. 17, 2014", 4 pgs.
(Continued)

*Primary Examiner* — Christopher D Prone
(74) *Attorney, Agent, or Firm* — Schwegman Lundberg & Woessner, P.A.

(57) ABSTRACT

Systems for determining force balance on a knee joint during a surgical procedure are disclosed. A system can include a tibial prosthesis. The tibial prosthesis can include a bearing component, a base component, and a shim component. The bearing component can have a superior articulating surface and an inferior surface. The bearing component can include a top portion, a bottom portion, a frame disposed between the top portion and the bottom portion, and a plurality of sensors disposed between the frame and the bottom portion. The frame can have a plurality of apertures corresponding in size or shape to the plurality of sensors. The base component can have a superior surface and an inferior surface. The shim component can be configured to be slidable between the inferior surface of the bearing component and the superior surface of the base component in an anterior to posterior direction.

16 Claims, 28 Drawing Sheets

(51) Int. Cl.
*A61B 5/103* (2006.01)
*A61B 17/02* (2006.01)

(52) U.S. Cl.
CPC .... *A61F 2/4657* (2013.01); *A61B 2017/0268* (2013.01); *A61B 2090/061* (2016.02); *A61F 2002/4661* (2013.01); *A61F 2002/4666* (2013.01)

(56) References Cited

U.S. PATENT DOCUMENTS

| | | | |
|---|---|---|---|
| 5,197,488 | A | 3/1993 | Kovacevic |
| 5,344,461 | A | 9/1994 | Phlipot |
| 5,360,016 | A | 11/1994 | Kovacevic |
| 5,364,402 | A | 11/1994 | Mumme et al. |
| 5,387,239 | A | 2/1995 | Bianco et al. |
| 5,395,401 | A | 3/1995 | Bahler |
| 5,425,775 | A | 6/1995 | Kovacevic et al. |
| 5,458,637 | A | 10/1995 | Hayes |
| 5,470,354 | A | 11/1995 | Hershberger et al. |
| 5,489,311 | A | 2/1996 | Cipolletti |
| 5,571,194 | A | 11/1996 | Gabriel |
| 5,609,645 | A | 3/1997 | Vinciguerra |
| 5,656,785 | A | 8/1997 | Trainor et al. |
| 5,658,341 | A | 8/1997 | Delfosse |
| 5,702,464 | A | 12/1997 | Lackey et al. |
| 5,733,292 | A | 3/1998 | Gustilo et al. |
| 5,776,200 | A | 7/1998 | Johnson et al. |
| 5,782,925 | A | 7/1998 | Collazo et al. |
| 5,824,103 | A | 10/1998 | Williams et al. |
| 5,871,541 | A | 2/1999 | Gerber |
| 5,976,147 | A | 11/1999 | LaSalle et al. |
| 6,126,692 | A | 10/2000 | Robie et al. |
| 6,607,559 | B2 | 8/2003 | Ralph et al. |
| 6,632,225 | B2 | 10/2003 | Sanford et al. |
| 6,702,821 | B2 | 3/2004 | Bonutti |
| 6,743,258 | B1 | 6/2004 | Keller |
| 6,770,078 | B2 | 8/2004 | Bonutti |
| 6,942,670 | B2 | 9/2005 | Heldreth et al. |
| 6,974,481 | B1 | 12/2005 | Carson |
| 7,309,363 | B2 | 12/2007 | Dietz |
| 7,364,581 | B2 | 4/2008 | Michalowicz |
| 7,412,897 | B2 | 8/2008 | Crottet et al. |
| 7,442,196 | B2 | 10/2008 | Fisher et al. |
| 7,488,330 | B2 | 2/2009 | Stad |
| 7,547,327 | B2 | 6/2009 | Collazo |
| 7,575,602 | B2 | 8/2009 | Amirouche et al. |
| 7,578,821 | B2 | 8/2009 | Fisher et al. |
| 7,587,945 | B2 | 9/2009 | Crottet et al. |
| 7,591,854 | B2 | 9/2009 | Wasielewski |
| 7,632,283 | B2 | 12/2009 | Heldreth |
| 7,632,314 | B2 | 12/2009 | Dietz |
| 7,695,520 | B2 | 4/2010 | Metzger et al. |
| 7,837,691 | B2 | 11/2010 | Cordes et al. |
| 7,850,698 | B2 | 12/2010 | Straszheim-Morley et al. |
| 8,065,927 | B2 | 11/2011 | Crottet et al. |
| 8,141,437 | B2 | 3/2012 | Amirouche et al. |
| 8,197,549 | B2 | 6/2012 | Amirouche et al. |
| 8,211,041 | B2 | 7/2012 | Fisher et al. |
| 8,245,583 | B2 | 8/2012 | Stein |
| 8,491,589 | B2 | 7/2013 | Fisher et al. |
| 8,506,571 | B2 | 8/2013 | Chana et al. |
| 8,603,101 | B2 | 12/2013 | Claypool et al. |
| 9,011,459 | B2 | 4/2015 | Claypool et al. |
| 9,149,206 | B2 | 10/2015 | Claypool et al. |
| 2002/0058997 | A1 | 5/2002 | O'connor et al. |
| 2002/0072802 | A1 | 6/2002 | O'Neil et al. |
| 2004/0019382 | A1 | 1/2004 | Amirouche et al. |
| 2004/0059340 | A1 | 3/2004 | Serra et al. |
| 2004/0064191 | A1 | 4/2004 | Wasielewski |
| 2004/0122441 | A1 | 6/2004 | Muratsu |
| 2004/0167537 | A1 | 8/2004 | Errico et al. |
| 2004/0225368 | A1 | 11/2004 | Plumet et al. |
| 2005/0055102 | A1 | 3/2005 | Tornier et al. |
| 2005/0177170 | A1 | 8/2005 | Fisher et al. |
| 2005/0267485 | A1 | 12/2005 | Cordes et al. |
| 2006/0020343 | A1 | 1/2006 | Ek |
| 2006/0052782 | A1 | 3/2006 | Morgan et al. |
| 2006/0069436 | A1 | 3/2006 | Sutton et al. |
| 2006/0089653 | A1 | 4/2006 | Auger et al. |
| 2006/0111726 | A1 | 5/2006 | Felt et al. |
| 2006/0184176 | A1 | 8/2006 | Straszheim-Morley et al. |
| 2006/0189864 | A1 | 8/2006 | Paradis et al. |
| 2006/0190087 | A1 | 8/2006 | O'Connor |
| 2007/0123992 | A1 | 5/2007 | Sanford |
| 2007/0234819 | A1 | 10/2007 | Amirouche et al. |
| 2007/0239165 | A1 | 10/2007 | Amirouche |
| 2008/0051908 | A1 | 2/2008 | Angibaud et al. |
| 2008/0091273 | A1 | 4/2008 | Hazebrouck |
| 2008/0103603 | A1 | 5/2008 | Hintermann |
| 2009/0005708 | A1 | 1/2009 | Johanson et al. |
| 2009/0125114 | A1 | 5/2009 | May et al. |
| 2009/0204222 | A1 | 8/2009 | Burstein et al. |
| 2009/0259314 | A1 | 10/2009 | Linder-Ganz et al. |
| 2009/0264894 | A1 | 10/2009 | Wasielewski |
| 2009/0287310 | A1 | 11/2009 | Fisher et al. |
| 2009/0306787 | A1 | 12/2009 | Crabtree et al. |
| 2010/0010494 | A1 | 1/2010 | Quirno |
| 2010/0063595 | A1 | 3/2010 | Dietz |
| 2010/0076563 | A1 | 3/2010 | Otto et al. |
| 2010/0082111 | A1 | 4/2010 | Thomas |
| 2010/0100011 | A1 | 4/2010 | Roche |
| 2010/0198275 | A1 | 8/2010 | Chana et al. |
| 2010/0249660 | A1 | 9/2010 | Sherman et al. |
| 2010/0249789 | A1 | 9/2010 | Rock et al. |
| 2011/0100011 | A1 | 5/2011 | Staffend |
| 2012/0095563 | A1 | 4/2012 | Sanford et al. |
| 2012/0158152 | A1 | 6/2012 | Claypool et al. |
| 2012/0179069 | A1 | 7/2012 | Amirouche |
| 2012/0232429 | A1 | 9/2012 | Fischer et al. |
| 2012/0290088 | A1 | 11/2012 | Amirouche et al. |
| 2012/0310246 | A1 | 12/2012 | Belcher et al. |
| 2013/0013076 | A1 | 1/2013 | Fisher et al. |
| 2013/0079671 | A1* | 3/2013 | Stein .............. A61B 5/6878 600/587 |
| 2013/0096567 | A1 | 4/2013 | Fisher et al. |
| 2013/0102929 | A1 | 4/2013 | Haight et al. |
| 2013/0103038 | A1 | 4/2013 | Fischer et al. |
| 2013/0253378 | A1 | 9/2013 | Claypool et al. |
| 2013/0261757 | A1 | 10/2013 | Claypool et al. |
| 2013/0261758 | A1 | 10/2013 | Claypool et al. |
| 2014/0052269 | A1 | 2/2014 | Claypool et al. |
| 2014/0296859 | A1 | 10/2014 | Claypool et al. |
| 2015/0088140 | A1 | 3/2015 | Toler et al. |
| 2015/0190243 | A1 | 7/2015 | Claypool et al. |
| 2015/0359642 | A1 | 12/2015 | Claypool et al. |

FOREIGN PATENT DOCUMENTS

| | | |
|---|---|---|
| CN | 101522136 A | 9/2009 |
| CN | 101711701 A | 5/2010 |
| CN | 101835441 A | 9/2010 |
| CN | 102018584 A | 4/2011 |
| CN | 103370025 A | 10/2013 |
| CN | 103379880 A | 10/2013 |
| CN | 104379094 A | 2/2015 |
| CN | 104736105 A | 6/2015 |
| CN | 105055052 A | 11/2015 |
| EP | 0903125 A1 | 3/1999 |
| EP | 1132063 A2 | 9/2009 |
| EP | 2237177 A1 | 10/2010 |
| FR | 2824260 A1 | 11/2002 |
| JP | 61247449 A | 11/1986 |
| JP | 09289998 A | 11/1997 |
| JP | 2007054488 A | 3/2007 |
| JP | 2009245619 A | 10/2009 |
| JP | 2010240406 A | 10/2010 |
| JP | 2015512307 A | 4/2013 |
| JP | 2014505517 A | 3/2014 |
| JP | 2014508554 A | 4/2014 |
| JP | 2014239900 A | 12/2014 |
| JP | 2015513966 A | 5/2015 |
| WO | WO-2010022272 A1 | 2/2010 |
| WO | WO-2010023062 A2 | 3/2010 |

(56) References Cited

FOREIGN PATENT DOCUMENTS

| WO | WO-2011063123 A2 | 5/2011 |
|---|---|---|
| WO | WO-2012004580 A1 | 1/2012 |
| WO | WO-2012020460 A1 | 2/2012 |
| WO | WO-2012082628 A1 | 6/2012 |
| WO | WO-2013013094 A1 | 1/2013 |
| WO | WO-2013148954 A1 | 10/2013 |
| WO | WO-2013148960 A1 | 10/2013 |

OTHER PUBLICATIONS

"U.S. Appl. No. 13/836,665, Final Office Action mailed Jul. 25, 2014", 25 pgs.
"U.S. Appl. No. 13/837,774, Examiner Interview Summary mailed Jul. 22, 2014", 4 pgs.
"U.S. Appl. No. 13/837,774, Final Office Action mailed Jul. 28, 2014", 17 pgs.
"U.S. Appl. No. 14/063,032, Notice of Allowance mailed Dec. 19, 2014", 6 pgs.
"U.S. Appl. No. 14/063,032, Response filed Oct. 20, 2014 to Non-Final Office Action mailed Jun. 20, 2014", 9 pgs.
"U.S. Appl. No. 14/304,009, Preliminary Amendment Filed Jul. 31, 2014", 7 pgs.
"Canadian Application Serial No. 2,824,527, Office Action mailed Mar. 17, 2014", 2 pgs.
"Canadian Application Serial No. 2,824,527, Response filed Sep. 17, 2014 to Office Action mailed Mar. 17, 2014", 14 pgs.
"Chinese Application Serial No. 201180067430.X, Office Action mailed Aug. 28, 2014", (With English Translation), 8 pgs.
"International Application Serial No. PCT/US2013/034286, International Preliminary Report on Patentability mailed Oct. 9, 2014", 8 pgs.
"International Application Serial No. PCT/US2013/034293, International Preliminary Report on Patentability mailed Oct. 9, 2014", 9 pgs.
"U.S. Appl. No. 13/819,116, Non Final Office Action mailed Jun. 2, 2015", 14 pgs.
"U.S. Appl. No. 13/819,116, Response filed Mar. 27, 2015 to Restriction Requirement mailed Feb. 12, 2015", 11 pgs.
"U.S. Appl. No. 13/819,116, Response filed Jul. 16, 2015 to Non Final Office Action mailed Jun. 2, 2015", 22 pgs.
"U.S. Appl. No. 13/836,665, Notice of Allowance mailed Jun. 9, 2015", 10 pgs.
"U.S. Appl. No. 13/837,774, Non Final Office Action mailed Sep. 18, 2015", 16 pgs.
"U.S. Appl. No. 13/837,774, Response filed Jul. 7, 2015 to Restriction Requirement mailed May 20, 2015", 10 pgs.
"U.S. Appl. No. 13/837,774, Restriction Requirement mailed May 20, 2015", 6 pgs.
"U.S. Appl. No. 14/034,076, Non Final Office Action mailed Jun. 24, 2015", 11 pgs.
"U.S. Appl. No. 14/833,385, Preliminary Amendment filed Aug. 25, 2015", 6 pgs.
"Chinese Application Serial No. 201180067757.7, Office Action mailed Mar. 2, 2015", (W/ English Translation), 18 pgs.
"Chinese Application Serial No. 201380028572.4, Office Action mailed Aug. 13, 2015", (W/ English Translation), 16 pgs.
"Japanese Application Serial No. 2014-121515, Office Action mailed Jun. 2, 2015", (W/ English Translation), 10 pgs.
"U.S. Appl. No. 13/836,586, Express Abandonment filed May 30, 2014", 1 pg.
"U.S. Appl. No. 13/836,665, Response filed May 30, 2014 to Non-Final Office Action mailed Jan. 30, 2014", 21 pgs.
"U.S. Appl. No. 13/837,774, Response filed Jun. 10, 2014 to Non-Final Office Action mailed Feb. 20, 2014", 29 pgs.
"U.S. Appl. No. 14/063,032, Non Final Office Action mailed Jun. 20, 2014", 6 pgs.
"Japanese Application Serial No. 2013-544858, Request for Examination filed Feb. 4, 2014", (With English Translation), 14 pgs.
"U.S. Appl. No. 13/819,116, Preliminary Amendment filed Feb. 26, 2013", 8 pgs.
"U.S. Appl. No. 13/836,665, Non Final Office Action mailed Jan. 30, 2014", 21 pgs.
"U.S. Appl. No. 13/837,774, Non Final Office Action mailed Feb. 10, 2014", 33 pgs.
"U.S. Appl. No. 14/063,032, Preliminary Amendment filed Oct. 25, 2013", 3 pgs.
"Australian Application Serial No. 2011343440, First Examiner Report mailed Feb. 17, 2014", 3 pgs.
"Australian Application Serial No. 2011343440, Response filed Mar. 21, 2014 to Office Action mailed Feb. 17, 2014", 1 pg.
"Canadian Application Serial No. 2,821,927, Voluntary Amendment mailed Jun. 14, 2013", 7 pgs.
"Chinese Application Serial No. 201180067757.7, Voluntary Amendment mailed Feb. 14, 2014", 4 pgs.
"U.S. Appl. No. 13/087,610, Non Final Office Action mailed Feb. 26, 2013", 7 pgs.
"U.S. Appl. No. 13/087,610, Notice of Allowance mailed Jun. 28, 2013", 6 pgs.
"U.S. Appl. No. 13/087,610, Notice of Allowance mailed Oct. 8, 2013", 7 pgs.
"U.S. Appl. No. 13/087,610, Response filed May 24, 2013 to Non Final Office Action mailed Feb. 26, 2013", 15 pgs.
"International Application Serial No. PCT/US2011/064435, International Preliminary Report on Patentability mailed Jun. 27, 2013", 9 pgs.
"International Application Serial No. PCT/US2011/064435, Search Report mailed Jun. 21, 2012", 5 pgs.
"International Application Serial No. PCT/US2011/064435, Written Opinion mailed Jun. 21, 2012", 7 pgs.
"International Application Serial No. PCT/US2011/065683, International Preliminary Report on Patentability mailed Jun. 27, 2013", 11 pgs.
"International Application Serial No. PCT/US2011/065683, International Search Report mailed Apr. 24, 2012", 12 pgs.
"International Application Serial No. PCT/US2011/065683, Written Opinion mailed Apr. 24, 2012", 10 pgs.
"International Application Serial No. PCT/US2013/034286, International Search Report mailed Jun. 25, 2013", 6 pgs.
"International Application Serial No. PCT/US2013/034286, Written Opinion mailed Jun. 25, 2013", 6 pgs.
"International Application Serial No. PCT/US2013/034293, International Search Report mailed Jun. 25, 2013", 6 pgs.
"International Application Serial No. PCT/US2013/034293, Written Opinion mailed Jun. 25, 2013", 7 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
"U.S. Appl. No. 13/819,116, Restriction Requirement mailed Feb. 12, 2015", 7 pgs.
"U.S. Appl. No. 13/836,665, Response filed Jan. 23, 2015 to Final Office Action mailed Jul. 25, 2014", 25 pgs.
"U.S. Appl. No. 13/837,774, Response filed Jan. 28, 2015 to Final Office Action mailed Jul. 28, 2014", 16 pgs.
"U.S. Appl. No. 14/660,217, Preliminary Amendment filed Mar. 18, 2015", 9 pgs.

(56) References Cited

OTHER PUBLICATIONS

"Chinese Application Serial No. 201180067430.X, Response filed Jan. 4, 2015 to Office Action mailed Sep. 26, 2014", (W/ English Translation), 14 pgs.

"European Application Serial No. 11808493.8, Examination Notification Art. 94(3) mailed Feb. 20, 2015", 6 pgs.

"Australian Application Serial No. 2013238046, First Examiner Report mailed Nov. 26, 2015", 2 pgs.

"Australian Application Serial No. 2013238046, Response filed Feb. 2, 2016 to First Examiner Report mailed Nov. 26, 2015", 1 pg.

"Chinese Application Serial No. 201180067757.7, Office Action mailed Nov. 16, 2015", (W/ English Translation), 17 pgs.

"Chinese Application Serial No. 201180067757.7, Response filed Jun. 10, 2015 to Office Action mailed Mar. 2, 2015", (W/ English Translation), 13 pgs.

"Chinese Application Serial No. 201380028683.5, Office Action mailed Nov. 4, 2015", W/ English Translation, 16 pgs.

"European Application Serial No. 13716636.9, Communication Pursuant to Article 94(3) EPC mailed Nov. 16, 2015", 4 pgs.

"European Application Serial No. 13716636.9, Communication pursuant to Rules 161(1) and 162 EPC mailed Dec. 12, 2014", 2 pgs.

"European Application Serial No. 13716636.9, Response filed Jun. 22, 2015 to Communication pursuant to Rules 161(1) and 162 EPC mailed Dec. 12, 2014", 10 pgs.

"European Application Serial No. 14190180.1, Extended European Search Report mailed Sep. 24, 2015", 8 pgs.

"Japanese Application Serial No. 2013-544655, Office Action mailed Sep. 29, 2015", (W/ English Translation), 7 pgs.

"Japanese Application Serial No. 2013-544655, Response filed Jan. 4, 2016 to Office Action mailed Sep. 29, 2015", (English Translation of Claims), 14 pgs.

"Japanese Application Serial No. 2014-121515, Notice of Reasons for Rejection mailed Jan. 5, 2016", (W/ English Translation), 9 pgs.

\* cited by examiner

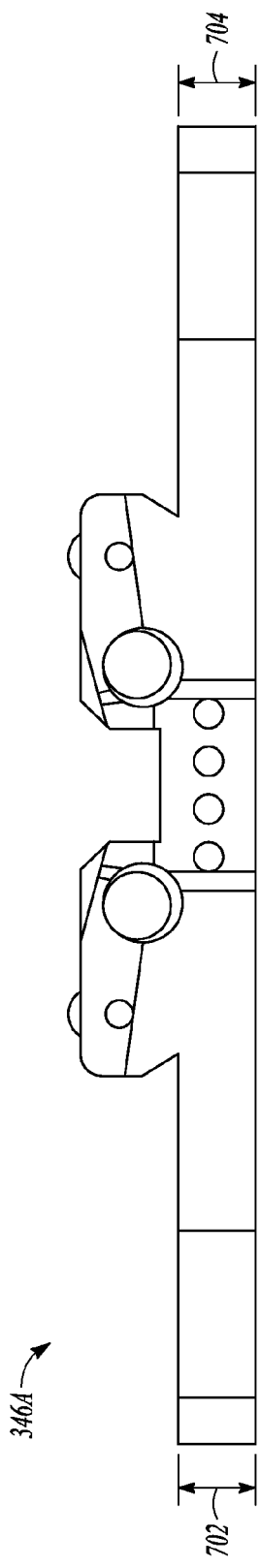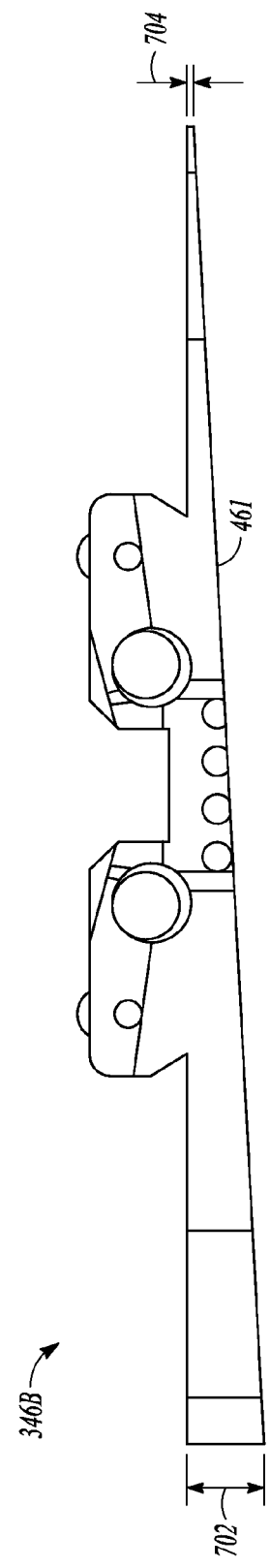

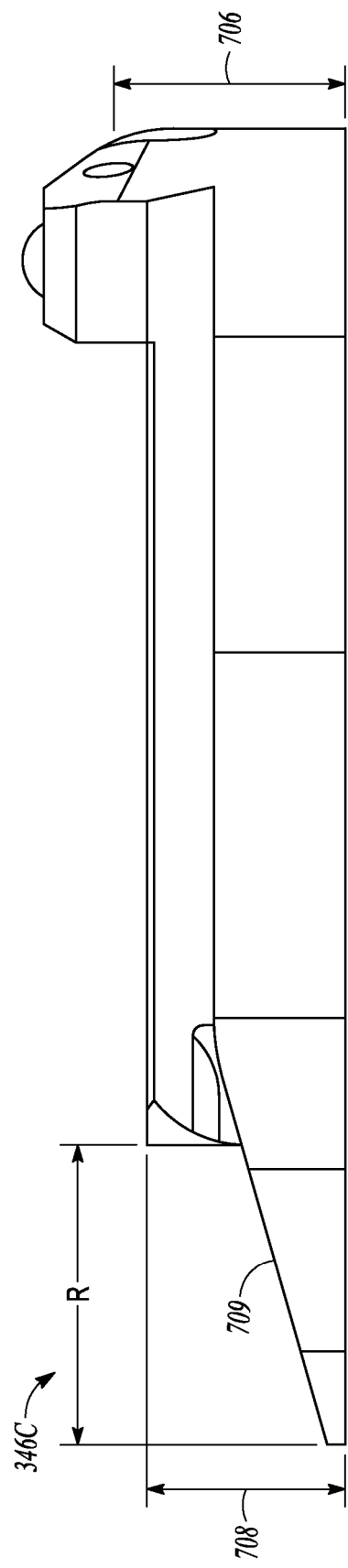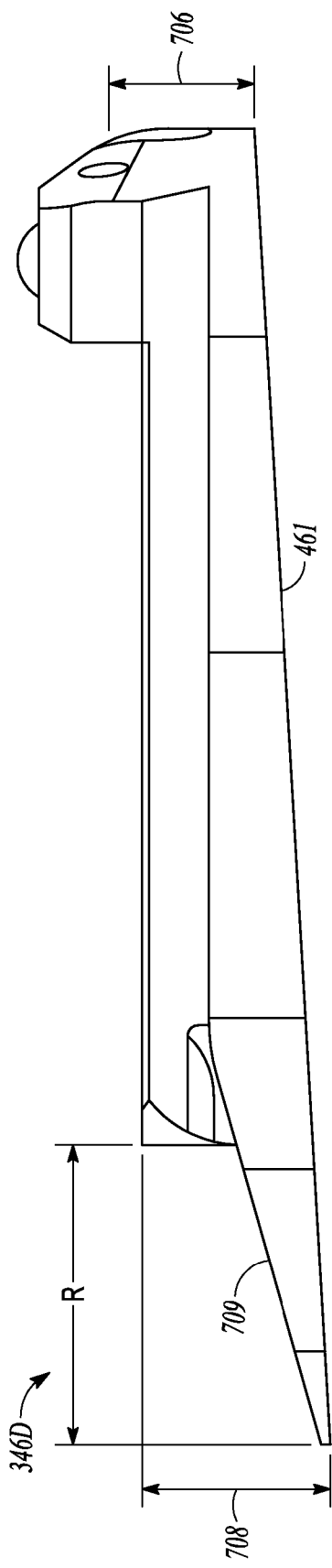

TIBIAL PROSTHESIS SYSTEMS, KITS, AND METHODS

CLAIM OF PRIORITY

This application claims the benefit of priority under 35 U.S.C. §119(e) of Claypool et al., U.S. Provisional Patent Application Ser. No. 61/618,376, entitled "TIBIAL PROSTHESIS SYSTEMS, KITS, AND METHODS," filed on Mar. 30, 2012, and also claims the benefit of priority under 35 U.S.C. §119(e) of Claypool et al., U.S. Provisional Patent Application Ser. No. 61/740,268, entitled "TIBIAL PROSTHESIS SYSTEMS, KITS, AND METHODS," filed on Dec. 20, 2012, each of which is herein incorporated by reference in its entirety.

TECHNICAL FIELD

This patent document pertains generally to tibial prosthesis systems, kits, and methods.

BACKGROUND

Provisional knee prosthesis systems, including a plurality of provisional components, can be positioned on a distal end of a femur or a proximal end of a tibia to allow a surgeon to test and appropriately fit a permanent knee prosthesis system within a patient. During surgery, the surgeon can remove and replace a provisional component having a first uniform thickness with a provisional component having a second uniform thickness to arrive at an appropriate configuration of the permanent knee prosthesis system.

OVERVIEW

This patent document pertains generally to provisional tibial prosthesis systems, kits, and methods, including one or more provisional tibial components that can collectively be used to replicate permanent (or final) tibial components or mimic bone cuts believed to be necessary during a surgical procedure. It is believed that the provisional tibial components can also be designed for, or find use as, permanent tibial components. Thus, while this disclosure relates to provisional uses of the present tibial prosthesis systems, kits, and methods, it should be appreciated that such subject matter can also find use in permanent applications. When used provisionally, the tibial prosthesis systems, kits, and methods disclosed herein can assist in determining a proper bone cut angle to be made (e.g., to a tibia or a femur) or a size, shape, or other configuration of a permanent tibial prosthesis system that is designed to replace all or a portion of a knee joint. The present tibial prosthesis systems, kits, and methods can be used in conjunction with one or both of a permanent tibial prosthesis system, as disclosed in U.S. Provisional Patent Application Ser. No. 61/381,800, filed on Sep. 10, 2010 and entitled "TIBIAL PROSTHESIS FACILITATING ROTATIONAL ALIGNMENT," or a shim handling instrument and user-interface, as disclosed in U.S. Provisional Patent Application Ser. No. 61/424,222, filed on Dec. 17, 2010 and entitled "USER INTERFACE RELATED TO A SURGICAL PROVISIONAL," the entire disclosures of each of which are hereby expressly incorporated by reference herein.

The present inventors recognize, among other things, that existing provisional systems, kits, and methods fail to provide a surgeon with insight of knee joint kinematics if an angled bone cut (e.g., a bone cut that is not parallel to a joint line of the knee) is made to a proximal end of the tibia or a distal end of the femur. The present inventors further recognize that existing provisional systems, kits, and methods require the stacking of a high number of provisional components to arrive at an appropriate configuration of the permanent tibial prosthesis system or fail to provide sensed force or pressure data providing a real-time indication of provisional knee joint balance.

The present shim components, which can include one or both of a medial edge having a different height than a lateral edge or an anterior edge having a different height than a posterior edge, advantageously provide a surgeon with knee joint kinematic insight regarding an angled bone cut before the cut is made and can reduce the number of provisional components needed for permanent system sizing. The present shim components can provide the surgeon with the ability to appropriately configure the tibia, the femur, and/or the permanent tibial prosthesis system to counterbalance a deficiency (e.g., varus, valgus, anterior/posterior, or posterior/anterior sloping) of the knee joint before making certain angled bone cuts and using a reduced number of provisional components.

A tibial prosthesis system can include a provisional bearing component, a bearing support component, such as a base or plate component, and the provisional shim component. The shim component can be inserted between an inferior surface of the bearing component and a superior surface of the bearing support component. The insertion of the shim component provides spacing adjustment between the bearing and bearing support components. A sensor can be coupled to or integrated with the bearing, bearing support, or shim components for real-time knee joint balance testing.

To further illustrate the systems disclosed herein, a non-limiting list of examples is provided here:

In Example 1, a system for determining force balance on a knee joint during a surgical procedure can comprise a tibial prosthesis. The tibial prosthesis can include a bearing component, a base component, and a shim component. The bearing component can have a superior articulating surface and an inferior surface. The bearing component can include a top portion, a bottom portion, a frame disposed between the top portion and the bottom portion, and a plurality of sensors disposed between the frame and the bottom portion. The frame can have a plurality of apertures corresponding in a size or shape to the plurality of sensors. The base component can have a superior surface and an inferior surface. The shim component can be configured to be slidable between the inferior surface of the bearing component and the superior surface of the base component in an anterior/posterior direction.

In Example 2, the system of Example 1 can optionally be configured such that the plurality of sensors is positioned on a plate disposed between the frame and the bottom portion.

In Example 3, the system of Example 2 can optionally be configured such that the plurality of sensors occupies a substantial portion of the plate such that the sensors align with a substantial portion of the superior articulating surface of the bearing component.

In Example 4, the system of any one or any combination of Examples 1-3 can optionally be configured such that the plurality of sensors is selected from the group consisting of piezoelectric sensors, force sensing resistors, strain gauges, force gauges, load cells, potentiometers, barometers, other pressure sensors, and other force sensors.

In Example 5, the system of any one or any combination of Examples 1-4 can optionally further comprise a user interface providing a representation of an area or volume of the tibial prosthesis for presentation on a display, the representation comprising a medial/lateral indication and an anterior/posterior indication.

In Example 6, the system of Example 5 can optionally further comprise a wired or wireless connection between the plurality of sensors and the user interface.

In Example 7, the system of any one or any combination of Examples 5 or 6 can optionally be configured such that the user interface includes at least one force center indicator for presentation on the display and based on sensed force or pressure data and sensor locations from at least a first subset of the plurality of sensors, and the at least one force center indicator is indicative of balance or imbalance between force or pressure levels on the knee joint.

In Example 8, the system of any one or any combination of Examples 5-7 can optionally further comprise a processor, configured to receive and process information from the plurality of sensors, in communication with the user interface.

In Example 9, the system of Example 8 can optionally be configured such that the processor is included in the tibial prosthesis.

In Example 10, the system of any one or any combination of Examples 1-9 can optionally further comprise a plurality of distinct projections sized and shaped to fit within the plurality of apertures of the frame and positioned between a superior articulating surface and an inferior surface of the bearing component.

In Example 11, the system of Example 10 can optionally be configured such that each of the plurality of distinct projections operatively engages with one of the plurality of sensors.

In Example 12, the system of any one or any combination of Examples 1-11 can optionally be configured such that the shim component is selected from a plurality of shims based on a proximal/distal spacing between the bearing component and the base component.

In Example 13, the system of Example 12 can optionally be configured such that the plurality of shims includes different-sized shims and at least one shim includes one or both of a medial edge having a different height than a lateral edge or an anterior edge having a different height than a posterior edge.

In Example 14, a system for determining force balance on a knee joint during a surgical procedure can comprise a tibial prosthesis. The tibial prosthesis can include a bearing component, a base component, and a set of shim components. The bearing component can have a superior articulating surface and an inferior surface and comprise a plurality of sensors. The base component can have a superior surface and an inferior surface. The at least one shim in the set of shim components can include one or both of a medial edge having a different height than a lateral edge or an anterior edge having a different height than a posterior edge. The one or more shims can be selected for insertion between the inferior surface of the bearing component and the superior surface of the base component in an anterior/posterior direction, based on a proximal/distal spacing between the bearing component and the base component.

In Example 15, the system of Example 14 can optionally be configured such that the bearing component further comprises a plate adapted to hold the plurality of sensors.

In Example 16, the system of Example 15 can optionally be configured such that the bearing component further comprises a top portion, a bottom portion, and a frame, disposed between the top portion and the bottom portion, having a plurality of apertures corresponding in a size or shape to the plurality of sensors. The plate can be disposed between the frame and the bottom portion.

In Example 17, the system of any one or any combination of Examples 14-16 can optionally be configured such that the plurality of sensors is selected from the group consisting of piezoelectric sensors, force sensing resistors, strain gauges, force gauges, load cells, potentiometers, barometers, other pressure sensors, and other force sensors.

In Example 18, the system of any one or any combination of Examples 14-17 can optionally further comprise a user interface providing a representation of an area or volume of the tibial prosthesis for presentation on a display, the representation comprising a medial/lateral indication and an anterior/posterior indication.

In Example 19, the system of Example 18 can optionally further comprise a wired or wireless connection between the plurality of sensors and the user interface. The user interface can include at least one force center indicator for presentation on the display and based on sensed force or pressure data and sensor locations from at least a first subset of the plurality of sensors. The at least one force center indicator can be indicative of balance or imbalance on the knee joint.

In Example 20, the system of any one or any combination of Examples 14-19 can optionally further comprise a provisional femoral prosthesis.

In Example 21, the system of any one or any combination of Examples 14-20 can optionally further comprise a handling instrument configured to engage with at least one component of the tibial prosthesis during an insertion of the tibial prosthesis in the knee joint.

In Example 22, a system for determining force balance on a knee joint during a surgical procedure can comprise a tibial prosthesis including a plurality of sensors, at least one shim component, a user interface, and a connection between the user interface and the plurality of sensors. The tibial prosthesis can further include a bearing component and a base component. The bearing component can have a superior articulating surface and an inferior surface, and comprise a top portion, a bottom portion, a frame disposed between the top portion and the bottom portion, and the plurality of sensors disposed between the frame and the bottom portion. The frame can have a plurality of apertures corresponding in a size or shape to the plurality of sensors. The base component can have a superior surface and an inferior surface. The at least one shim component can be configured to be slidable between the inferior surface of the bearing component and the superior surface of the base component in an anterior/posterior direction. The at least one shim component can be selected from a plurality of shim components of varying sizes. The user interface can have a representation of an area or volume of the tibial prosthesis for presentation on a display. The connection can be configured such that the user interface receives information from the plurality of sensors and provides at least one force center indicator of balance or imbalance on the knee joint for presentation on the display.

In Example 23, the system of Example 22 can optionally be configured such that the plurality of shim components of varying sizes includes a plurality of shim components having one or both of a medial edge having a different height than a lateral edge or an anterior edge having a different height than a posterior edge.

In Example 24, the system of any one or any combination of Examples 22 or 23 can optionally be configured such that the at least one shim component includes a first shim and a second shim. Each of the shims can be slidable between the inferior surface of the bearing component and the superior surface of the base component after the tibial prosthesis is inserted in the knee joint.

In Example 25, the system of any one or any combination of Examples 22-24 can optionally be configured such that the user interface comprises a plurality of sensor icons for presentation on the display. The sensor icons can have locations on the display corresponding to a relative location of the sensors within the bearing component.

In Example 26, the system of any one or any combination of Examples 22-25 can optionally be configured such that the connection between the user interface and the plurality of sensors includes a processor and a computing device. The processor can be configured to receive and process force or pressure data from the plurality of sensors. The computing device can be configured to receive the force or pressure data from the processor. The processor and the computer device can communicate wirelessly.

In Example 27, the system of any one or any combination of Examples 1-26 can optionally be configured such that all elements or options recited are available to use or select from.

These and other examples and features of the present systems will be set forth in part in the following Detailed Description. This Overview is intended to provide non-limiting examples of the present subject matter—it is not intended to provide an exclusive or exhaustive explanation. The Detailed Description below is included to provide further information about the present tibial prosthesis systems, kits, and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present document.

FIGS. 7-8 illustrate front views of a shim component of a tibial prosthesis system, as constructed in accordance with at least two embodiments.

FIGS. 9-10 illustrate side views of a shim component of a tibial prosthesis system, as constructed in accordance with at least two embodiments.

DETAILED DESCRIPTION

The present inventors recognize that it can be desirable to provide surgeons with knee joint kinematic insight before certain bone cuts are made (e.g., to a tibia or a femur) and with the ability to quickly create a configuration appropriate for a permanent tibial prosthesis system using provisional components. The present tibial prosthesis systems, kits, and methods can include a provisional bearing component, a bearing support component, such as a base component or a plate component, and a provisional shim component. The shim component can include one or both of a medial edge having a different height than a lateral edge or an anterior edge having a different height than a posterior edge and can be inserted between the bearing component and the bearing support component. The differing height profile of the shim component can provide a surgeon with knee joint kinematic insight regarding an angled bone cut before the cut is made and can allow for sizing of an appropriate permanent prosthesis component configuration using a reduced number of provisional components. A sensor can be coupled to or integrated with the bearing, bearing support, or shim components for real-time knee joint balance testing.

Figure 1:
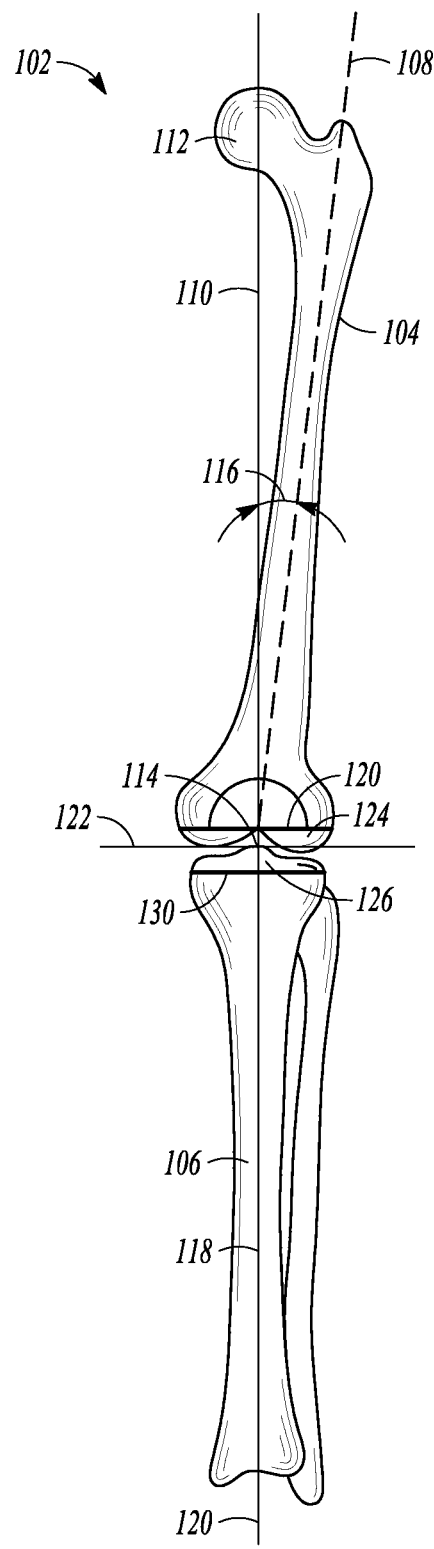
FIGS. 1-2 illustrate knee joint structures providing suitable environments in which a tibial prosthesis system, as constructed in accordance with at least one embodiment, can be used.
Figure 2:
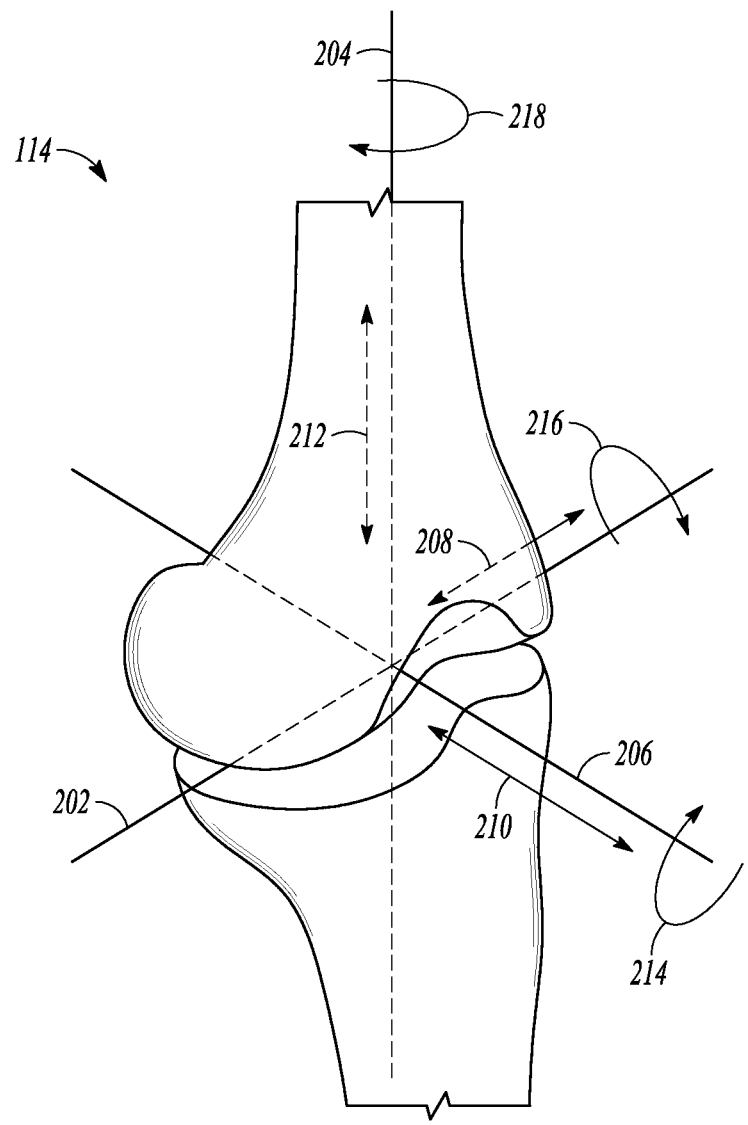

To better understand knee joint replacement procedures, it can be helpful to understand the relationship of bones and bone cuts that can be made to orient various provisional and permanent prosthesis components within a knee joint. FIGS. 1 and 2 illustrate several features of knee joint structures and orientations. In FIG. 1, a frontal view of a lower limb 102, including a femur 104 and a tibia 106, is shown to illustrate various lower limb axes. The femur 104 has an anatomic axis 108 that coincides generally with its intramedullary canal. The femur 104 also has a mechanical axis 110, or load axis, running from the center of a femoral head 112 to the center of a knee joint 114. The angle 116 extending between these two axes varies among the patient population, but is generally on the order of between 5-7 degrees, inclusive. Like the femur 104, the tibia 106 also has an anatomic axis coinciding generally with its intramedullary canal. The mechanical axis 118 of the tibia 106 runs from the center of the knee joint 114 to the center of an ankle region 120 and is generally collinear with its anatomic axis.

A joint line 122, about which the knee joint 114 flexes, is approximately parallel to a line through medial and lateral femoral condyles 124 and to a tibial plateau 126. Although illustrated as perpendicular in FIG. 1, the joint line 122 can extend at a varus or valgus angle relative to the mechanical axes 110 and 118 of the femur 104 and tibia 106, respectively. Normally, during a partial or total knee replacement procedure, portions of a distal end of the femur 104 or a proximal end of the tibia 106 are resected to be parallel or approximately parallel to the joint line 122, and thus perpendicular to the mechanical axes 110 and 118, as indicated at 128 and 130, respectively.

FIG. 2 illustrates a closer view of the knee joint 114 and its coordinate system, in which a medial/lateral axis 202 corresponds approximately to the joint line 122 (FIG. 1), a proximal/distal axis 204 corresponds approximately to the mechanical axes 110 and 118 (FIG. 1), and an anterior/posterior axis 206 is approximately normal to the other two axes. Position along each of these axes can be depicted by arrows, which can represent the medial/lateral 208, anterior/posterior 210, and proximal/distal 212 positioning of inserted prosthesis components. Rotation about each of these axes can also be depicted by arrows. Rotation about the proximal/distal axis 204 can correspond anatomically to external rotation of a femoral component, while rotation about the anterior/posterior axis 206 and medial/lateral axis 202 can correspond to extension plane slope and varus/valgus angle of a component, respectively. Depending on a position of the proximal tibial cut 130 (FIG. 1) made, a varus/valgus angle 214, extension plane angle 216, external rotation 218, or joint extension gap can be affected. Similarly, a position of the distal femoral cut 128 (FIG. 1) can affect the location of the joint line 122, the extension gap, the varus/valgus angle 214, or the extension plane angle 216.

Figure 3:
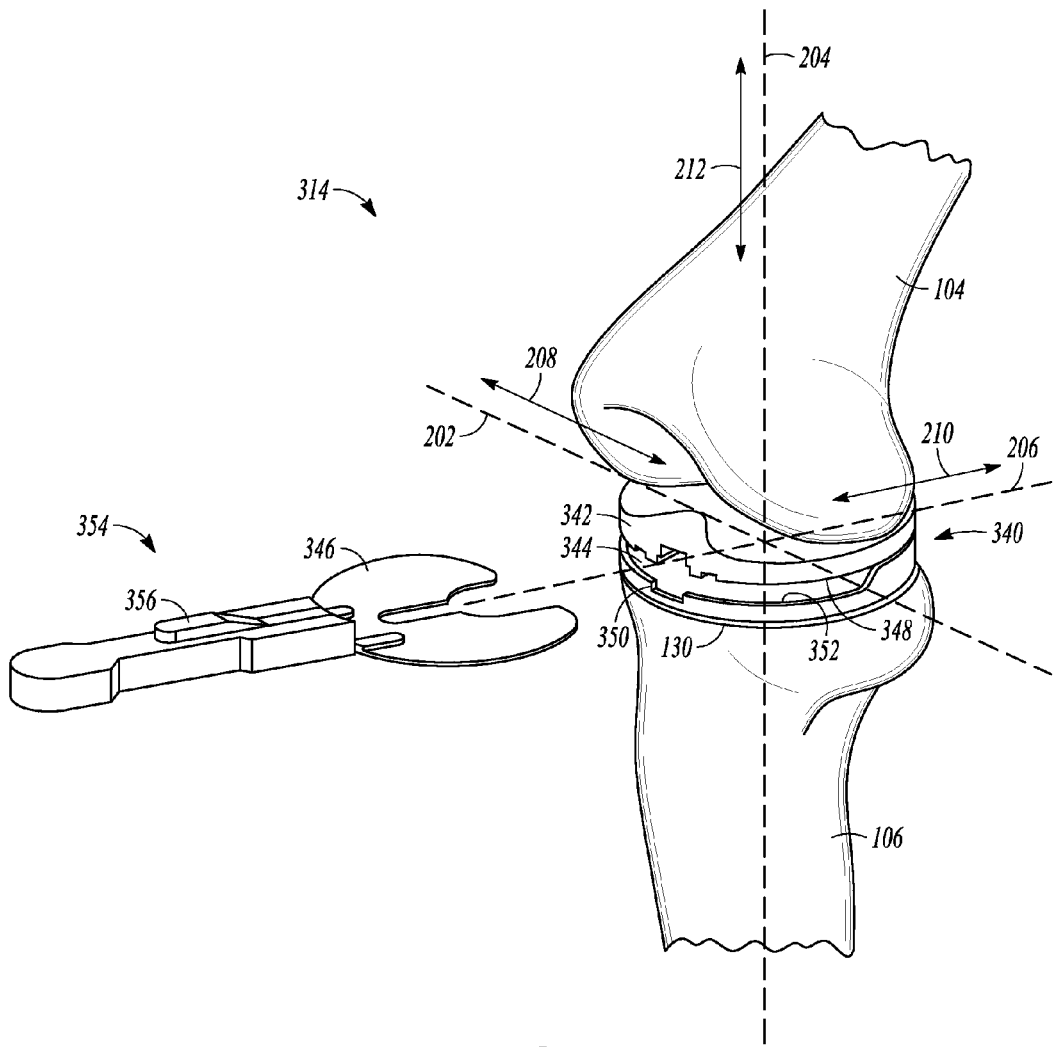
FIG. 3 illustrates a partially resected knee joint structure and a tibial prosthesis system, as constructed in accordance with at least one embodiment.

FIG. 3 illustrates a partially resected knee joint 314 structure, including a proximal tibial cut 130, and a provisional tibial prosthesis system 340. The provisional tibial prosthesis system 340 can include a bearing component 342, a base component 344, a plate component 350, and a shim component 346 insertable between an inferior surface 348 of the bearing component 342 and a superior surface 352 of the base component 344. The shim component 346 can include one or both of a medial edge having a different height than a lateral edge or an anterior edge having a different height than a posterior edge and can be used as a height varying spacer block between the bearing component 342 and the base component 344. The spacing of the bearing component 342 from the base component 344, for example, is adjustable to allow for representation of a variety of different sized angled bone cuts that can be made to a femur 104 or a tibia 106 or permanent tibial prosthesis systems. The shim component 346 can be inserted between the inferior surface 348 of the bearing component 342 and the superior surface 352 of the base component 344 using a shim handling instrument 354. The shim handling instrument 354 can include a release means 356 to disengage the shim component 346 after its insertion between the bearing 342 and base 344 components.

Figure 4A:
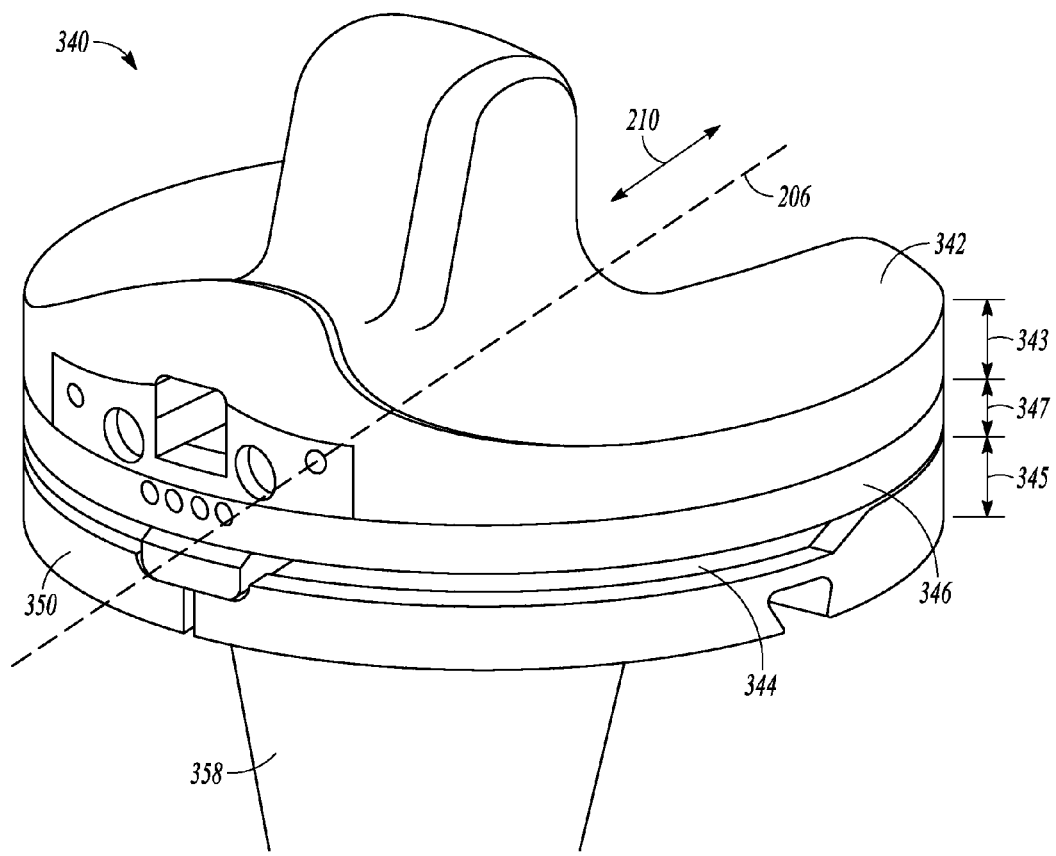
FIGS. 4A-4B respectively illustrate assembled and component views of a tibial prosthesis system, as constructed in accordance with at least one embodiment.
Figure 4B:
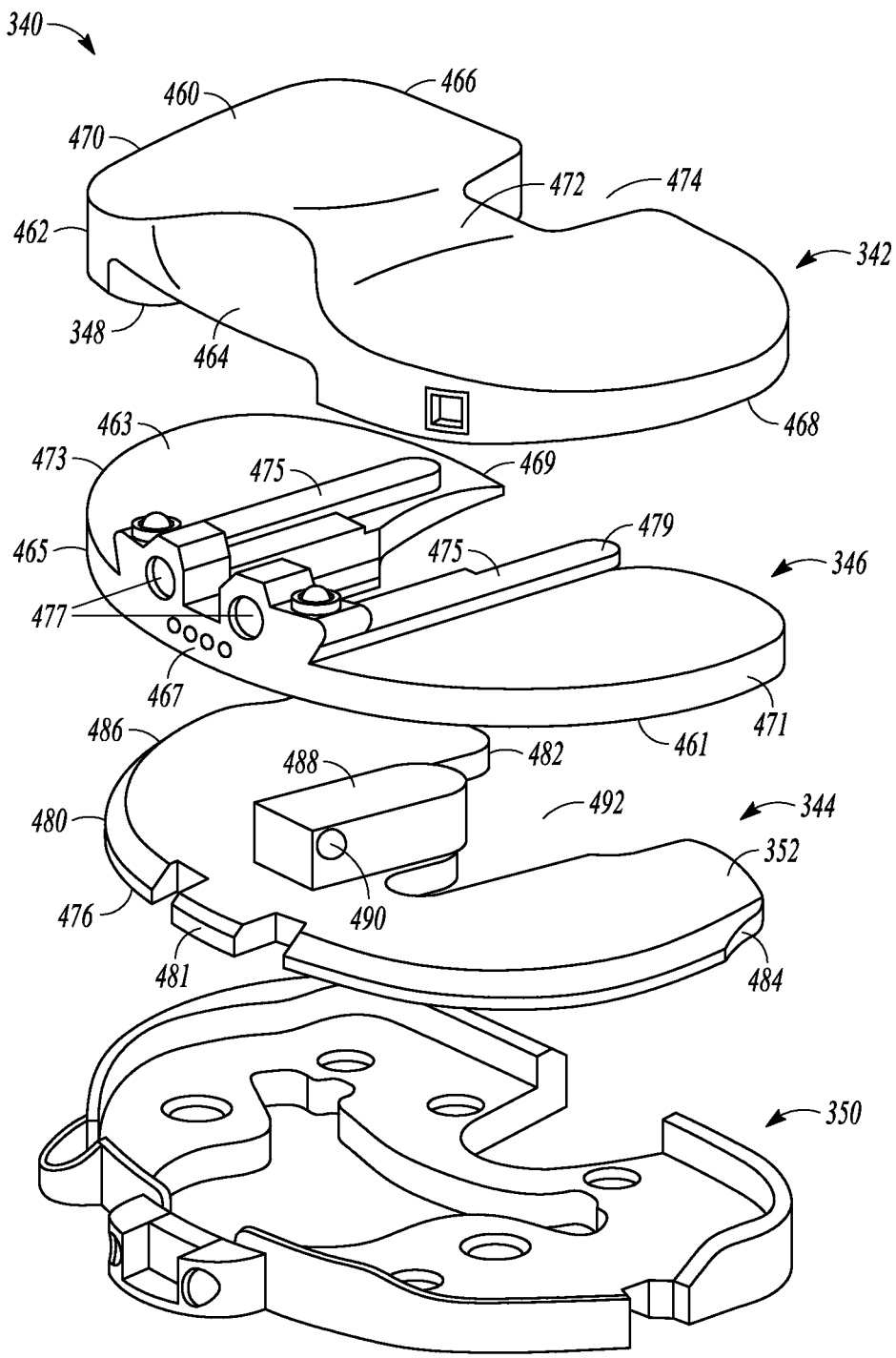

FIGS. 4A and 4B respectively illustrate assembled and component views of a provisional tibial prosthesis system 340. The provisional tibial prosthesis system 340, or components thereof, can be used to mimic geometry of one or both of an angle bone cut to be made or a permanent tibial prosthesis system. For example, the assembled tibial prosthesis system 340 of FIG. 4A, illustrates a bearing component 342, a shim component 346, a base component 344, and a plate component 350. A stem component 358 can be attached to the plate component 350 and used to secure the plate component 350 to a resected tibia 106 (FIG. 3).

Each component of the provisional tibial prosthesis system 340 includes an associated height. A shim component height 347 can be combined with a bearing component height 343 and a base component height 345, for example, to represent a desired height of a permanent tibial prosthesis system. A plurality of different or varying sized shims 346 can be slidably inserted between the bearing component 342 and a bearing support component, such as the base component 344, in an anterior/posterior 210 direction. Advantageously, the different or varying sized shims 346 can be inserted and removed without removing the bearing component 342 or the bearing support component from within a knee joint 314 (FIG. 3). Instead, all that is needed is a distraction of the knee joint 314 in an amount equal or approximately equal to the height profile of a particular shim component 346. In one example, the shim handling instrument 354 can be used to engage one or more handling alignment voids of a shim component 346 to assist in inserting and removing the shim component 346 between the bearing component 342 and the bearing support component 344. The one or more handling alignment voids of the shim component 346 can be consistent over the broad range of different sized shim components for universal compatibility with the shim handling instrument 354.

Each component of the provisional tibial prosthesis system 340 can include a structure defined by various surfaces, voids, or cavities. As shown in FIG. 4B, the bearing component 342, for example, can include an inferior surface 348, an opposing superior surface 460, and a peripheral wall 462 extending from the inferior surface 348 to the superior surface 460. The bearing component 342 can further include an anterior side 464, a posterior side 466, a lateral side 468, and a medial side 470. The superior surface 460 can be configured to articulate with natural or prosthetic condyles of a distal femur and can include a bearing lateral articular surface portion and a bearing medial articular surface portion, with a central tibial eminence 472 disposed between the articular surface portions. The inferior surface 348 can include a bearing cavity and one or more bearing nub cavities. The bearing cavity can extend from the inferior surface 348 toward the superior surface 460 and can be sized and shaped to accept a projection of the base component 344. The bearing nub cavities can extend on opposing sides of the bearing cavity and can each be sized and shaped to receive a nub located on the projection of the base component 344.

A posterior cruciate ligament (PCL) cutout 474 can be disposed at the posterior side 466 between the articular surfaces. The PCL cutout 474 can be sized and positioned to correspond with a PCL of the knee joint 314. In the example of FIG. 4B, the bearing component 342 is illustrated as a cruciate retaining bearing component, although it is contemplated that other tibial bearing components can be used. Bearing components that cooperate to form a posterior stabilized prosthesis, as shown in the example of FIG. 4A, or a knee prosthesis having an intermediate level of constraint between a posterior stabilized and cruciate retaining prosthesis are within the scope of the present disclosure. The bearing component 342 can also be made available in a variety of shapes and sizes to accommodate a variety of patient knee joints.

The base component 344 can include an inferior surface 476, an opposing superior surface 352, and a peripheral wall 480 extending from the inferior surface 476 to the superior surface 352. The base component 344 can further include an anterior side 481, a posterior side 482, a lateral side 484, and a medial side 486. A projection 488, including one or more nubs 490, can extend from the superior surface 352. The projection 488 and nubs 490 can be configured to be received within, and couple to, the bearing and bearing nub cavities of the bearing component 342. The base component 344 can include one or more of a W-shaped notch 492 at the posterior side 482, an undercut portion to mate with a raised perimeter of the plate component 350, a medial side groove, and a lateral side groove.

The bearing component 342 and the base component 344 can be coupled to or engaged with each other. In an example, the bearing component 342 can be positioned atop of the base component 344 and the projection 488, including the one or more nubs 490, of the base component 344 can be positioned within the bearing and bearing nub cavities of the bearing component 342. The base component 344 can be secured to the bearing component 342 in a medial/lateral direction 208 (FIG. 2) when the projection 488 is received with the bearing cavity and can be secured in an anterior/posterior direction 210 (FIG. 2) when the one or more nubs 490 are received with respective nub cavities. The walls of the bearing cavity can provide a physical barrier to inhibit significant relative movement between the base component 344 and the bearing component 342 in the medial/lateral direction 208. Similarly, the walls of the bearing nub cavities can provide a physical barrier to inhibit significant relative movement between the base component 344 and the bearing component 342 in the anterior/posterior direction 210. When the bearing component 342 is positioned atop the base component 344, and before insertion of the shim component 346, the bearing component can 342 be movable relative to the base component 344 in a proximal/distal direction 212 (FIG. 2).

As further discussed with respect to and illustrated in FIGS. 11 and 12, below, the base component 344 can be secured to the base plate 350, such that the base component 344 is located between the bearing component 342 and the base plate 350.

Turning again to FIG. 4B, the shim component 346 can include an inferior surface 461, an opposing superior surface 463, and a peripheral wall 465 extending from the inferior surface 461 to the superior surface 463. The peripheral wall 465 can define an exterior profile of the shim component 346. In an example, the exterior profile of the shim component 346 can substantially match an exterior profile of the base component 344 or the plate component 350. The shim component 346 can further include an anterior side 467, a posterior side 469, a lateral side 471, and a medial side 473.

Figure 6A:
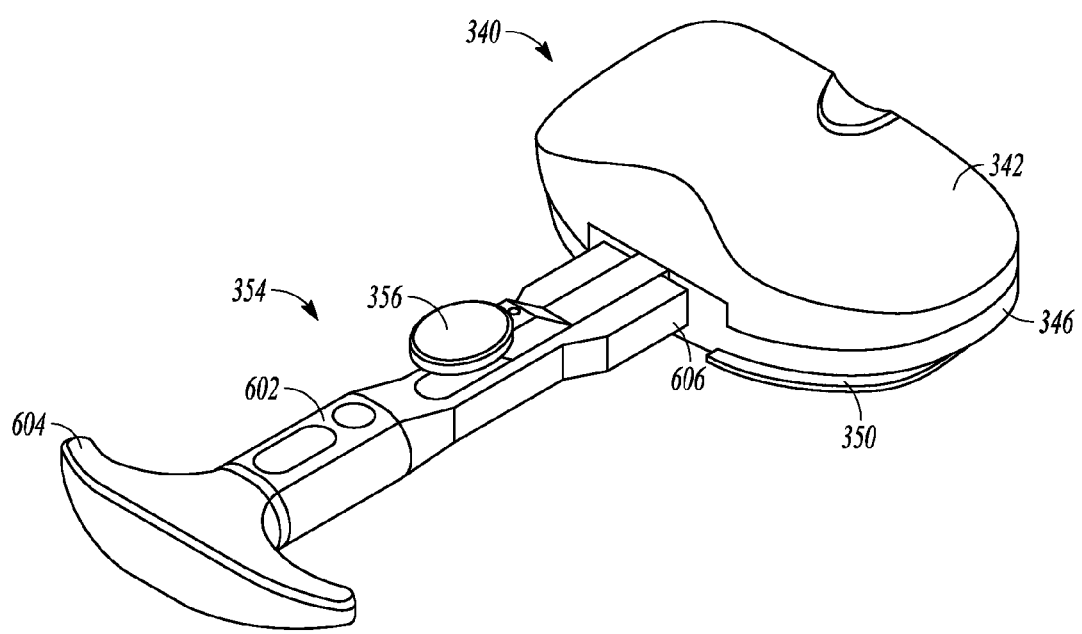
FIG. 6A-6B respectively illustrate assembled and component views of a tibial prosthesis system and a shim handling instrument, as constructed in accordance with at least one embodiment.

The superior surface 463 can include one or more rails 475 and one or more handling alignment voids 477. The one or more rails 475 can be configured to slidably engage one or more slots on the inferior surface 348 of the bearing component 342. The rails 475 can extend from the anterior side 467 toward the posterior side 469, such in an orientation parallel to the anterior/posterior direction 210. The rails 475 can include lead-in edges 479 to facilitate alignment and engagement with the slots of the bearing component 342. The rail 475/slot engagement between the shim component 346 and the bearing component 342 can inhibit lift-off the bearing component 342 from the shim component 346. The one or more handling alignment voids 477 can be configured to engage with an interface of a shim handling instrument, such as is shown in FIG. 6A.

A set of different sized shim components 346 can be provided in a kit to allow for varying levels of adjustment of the provisional tibial prosthesis system 340 and insight into knee joint kinematics if certain bone cuts are made to a tibia 106 (FIG. 1) or a femur 104 (FIG. 1). Particularly, the distance between the bearing component 342 and the base component 344 can be increased or decreased by inserting and removing different sized shim components 346. At least one of the shim components 346 can include one or both of a medial edge having a different height than a lateral edge or an anterior edge having a different height than a posterior edge. The medial edge height and the lateral edge height can be sized such that the inferior surface 461 of the shim component 346 includes a medial to lateral angle of between +3 degrees and −3 degrees, inclusive. The anterior edge height and the posterior edge height can be sized such that the inferior surface 461 of the shim component 346 includes an anterior to posterior angle of between +3 degrees and −3 degrees, inclusive. Two or more shim components 346 from the set can, in an example, be stacked to achieve desirable knee joint kinematics. It is believed that the set of different sized shim components 346 can include any desired number of shims having a constant or differing height.

Figure 5:
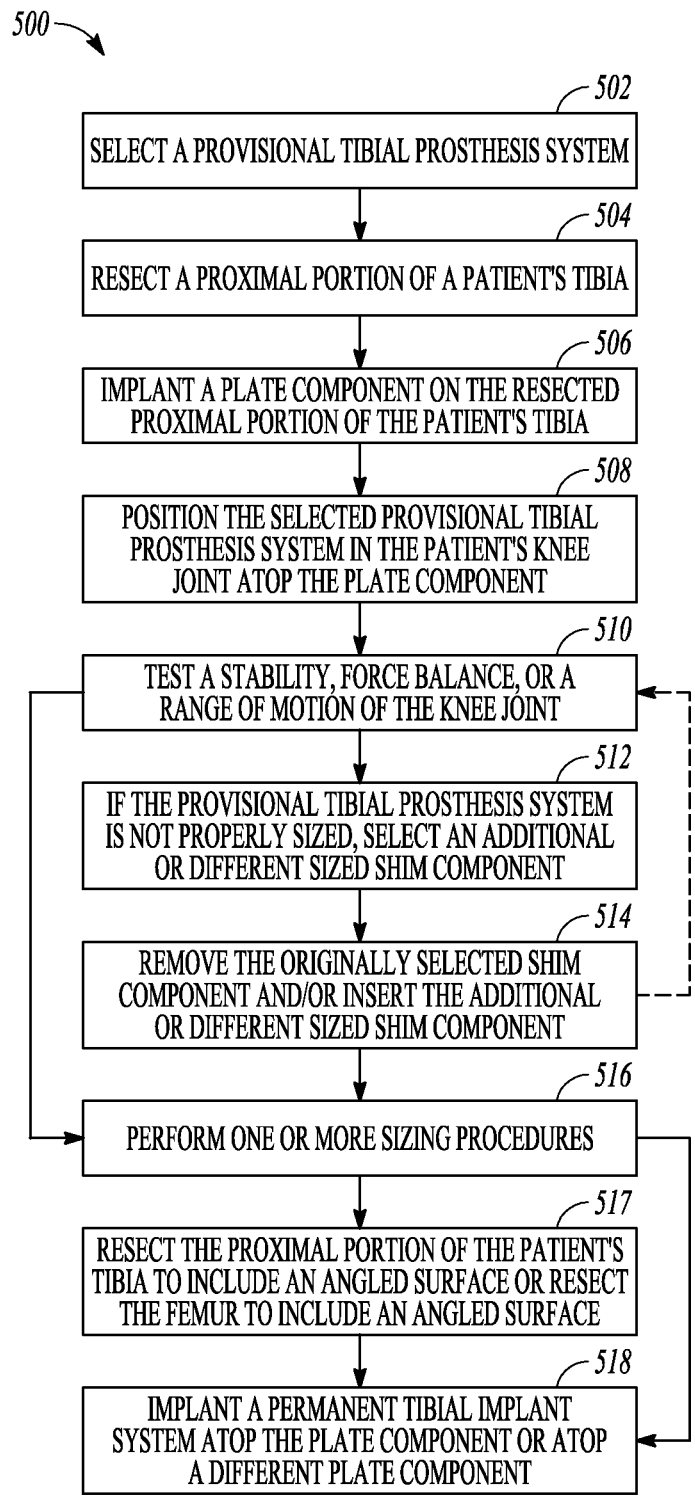
FIG. 5 illustrates a method of using a tibial prosthesis system, as constructed in accordance with at least one embodiment.

FIG. 5 illustrates a method 500 of using a provisional tibial prosthesis system to determine a proper angle of a bone cut to be made, if any, and an appropriate size (e.g., height) for a permanent tibial prosthesis system in a knee joint. At 502, a surgeon or other caregiver selects a particular size of the provisional tibial prosthesis system believed to be suitable for a patient. The provisional tibial prosthesis system can include a bearing member, a bearing support component, comprising one or both of a base component or a plate component, and a shim component. The plate component can include an inferior surface configured to contact a resected portion of a tibia and an opposing superior surface. The base component can include a base component height and be attachable to the plate component. The bearing component can include a bearing component height, and the shim component can include a shim component height. The shim component can be configured to be slidably received between the bearing component and the bearing support component in an anterior/posterior direction.

At 504, a proximal end portion of the patient's tibia is resected to be parallel or approximately parallel to a joint line of a knee. The tibia can be resected using standard surgical techniques to provide a substantially flat surface for receipt of the inferior, bone contacting surface of the plate component. Once the proximal end portion of the tibia is resected, the plate component can be implanted and secured to the resected tibia, at 506.

At 508, one or more of the selected bearing, shim, and base components can be positioned atop the plate component. In an example, the selected bearing and base components can initially be positioned atop the plate component, and subsequently, the selected shim component can be inserted between the bearing and base components in the anterior/posterior direction. The inserted shim component can include one or both of a medial edge having a different height than a lateral edge or an anterior edge having a different height than a posterior edge to counterbalance a deficiency (e.g., varus, valgus, anterior/posterior, or posterior/anterior sloping) of the knee joint.

At 510, the surgeon can perform one or more of a stability, a force balance, or a range of motion test of the knee joint to determine whether proper joint kinematics are present. The testing can include sensing at least one of a pressure, force, or position of the knee joint using a sensor coupled to or integrated with a provisional component. If the surgeon determines that proper knee joint kinematics is present, sizing procedures can begin, at 516. The sizing procedures can include determining whether an angled bone cut to the tibia and/or femur (e.g., a bone cut that is not parallel to the joint line of the knee) is needed, at 517, such as to counterbalance the knee joint deficiency, or determine the height of the provisional tibial prosthesis system. The angled bone cut to the tibia and/or femur can correspond to a height profile of the selected shim. The sizing procedures can use a sizing guide including alignment pins that fit in respective exterior voids in one or more provisional components to properly align the sizing guide to the components. Once properly aligned, a locking component of the sizing guide can slide along a shim ramp, for example, and, when the locking component slides past the shim ramp, a biasing force on the locking component can cause the locking component to travel downward and engage a backside of shim ramp to lock the sizing guide to the shim component.

At 512, if the provisional tibial prosthesis system is determined to not be properly sized due to improper joint kinematics being present, an additional or different sized shim component can be selected. At 514, the originally selected shim component can be removed from between the bearing component and the bearing support component and/or the newly selected shim component can be inserted between the bearing component and the bearing support component. The newly selected shim component can include at least one of a medial edge, a lateral edge, an anterior edge, or a posterior edge having a different height than the originally selected shim component. Insertion and removal of the shim components can be achieved in the anterior/posterior direction using a shim handling instrument. The bearing and bearing support components can be configured and coupled to each other in such a way that removal or insertion of shim components does not disturb the coupling arrangement.

With the newly selected shim component in place, the surgeon can again perform one or more of a stability, a force balance, or a range of motion test of the knee joint, at 510, to determine whether proper joint kinematics are present. Shim component replacement or stacking can be repeated, using a variety of different or similarly sized shims and a variety of different numbers of shims, until the surgeon determines that proper joint kinematics are present.

Finally, at 518, a permanent tibial prosthesis system can be selected and implanted. The permanent tibial prosthesis system can include a height that corresponds to the height of one or more provisional tibial prosthesis system components.

Figure 6B:
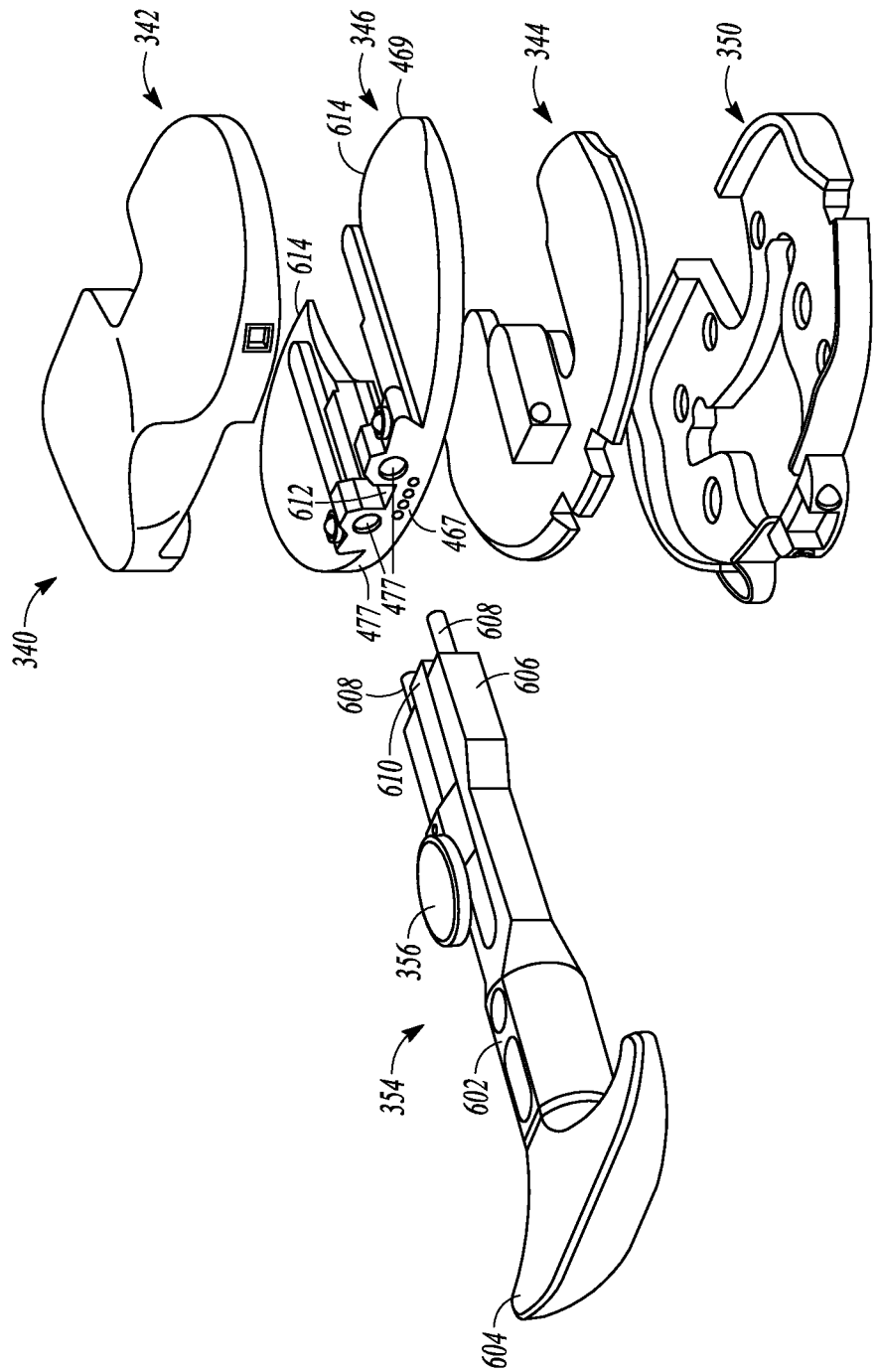

FIGS. 6A and 6B respectively illustrate assembled and component views of a provisional tibial prosthesis system 340 and a shim handling instrument 354 attachable to a shim component 346 of the system. As discussed with respect to FIG. 5, above, the shim handling instrument 354 can be used for insertion or removal of different sized shim components 346. The shim handling instrument 354 can include, among other things, a handle body 602, a user-engageable end 604, an opposing attachment end 606, one or more alignment pins 608, release means 356 (e.g., a release button), and an engageable tooth 610. The one or more alignment pins 608 can be positioned on each side of the engageable tooth 610. The alignment pins 608 can be configured to fit into respective handling alignment voids 477 positioned near an anterior side 467 of the shim component 346.

When the shim handling instrument 354 and the shim component 346 are properly aligned, the engageable tooth 610 can be configured to slide along a shim ramp 612. When the engageable tooth 610 slides along the shim ramp 612, a biasing force on the engageable tooth 610 can cause the tooth to travel downward and engage a backside of the shim ramp 612, thereby locking the shim handling instrument 354 to the shim component 346. The biasing force can be exerted on the engageable tooth 610 by a tension spring.

When the shim handling instrument 354 is locked to the shim component 346, a surgeon holding the user-engageable end 604 of the shim handling instrument 354 can insert the shim component 346 between a bearing component 342 and a bearing support component, such as one or both of a base component 344 or a plate component 350, in an anterior/posterior direction 210 (FIG. 2). The insertion of the shim component 346 can space the bearing component 342 from the bearing support component a distance equal to the shim component height 347 (FIG. 4A) along a proximal/distal axis 204 (FIG. 2). During insertion of the shim component 346, an entry ramp 614 on a posterior side 469 of the shim component 346 can be used to urge, in a ramp-like manner, separation of the bearing component 342 and the bearing support component. Once the shim component 346 is fully inserted between the bearing component 342 and the bearing support component, the release means 356 can be depressed to overcome the downward biasing force on the engageable tooth 610. In this way, the engageable tooth 610 can be disengaged from the backside of the shim ramp 612 and the shim handling instrument 354 can be disengaged from the shim component 346. In a similar manner, the shim handling instrument 354 can be used to remove the shim component 346 from between the bearing component 342 and the bearing support component.

Advantageously, the present provisional tibial prosthesis system 340 can be adjusted in a manner requiring a knee joint 114 (FIG. 2) to only be distracted by a distance equal to a height profile of the shim component 346. The shim components 346, as shown in FIGS. 8 and 10, can include one or both of a medial edge having a different height than a lateral edge or an anterior edge having a different height than a posterior edge. Differing height shim components 346 can advantageously provide a surgeon with joint kinematic insight regarding an angled bone cut before the cut is made, and can reduce the number of provisional components needed during surgery sizing by offering tailored separation between knee joint components. Also, the bearing component 342 and the bearing support component, such as the base component 344, do not have to be removed from the knee joint 114 to insert and remove shim components 346.

FIGS. 7 and 8 illustrate front views of at least two versions of a shim component of a provisional tibial prosthesis system. The shim component 346A of FIG. 7 includes a medial edge height 702 that is the same or substantially the same as a lateral edge height 704. In contrast, the shim component 346B of FIG. 8 includes a medial edge height 702 that is different than a lateral edge height 704. In the example shown, the medial edge height 702 is greater than the lateral edge height 704 and can be used by a surgeon to analyze possible bone cuts for a patient experiencing a varus (or bow-legged) knee joint. Alternatively, the medial edge height 702 can be less than the lateral edge height 704 and can be used by a surgeon to analyze possible bone cuts for a patient experiencing a valgus (for knock-kneed) joint. Due to a height difference between the medial and lateral edges, an inferior surface 461 of the shim component can include a medial to lateral angle of between +3 degrees and −3 degrees, inclusive. The wedge-like shape of the shim component 346B can be used by the surgeon to assess kinematics of a knee joint if a particular bone cut is made. In this way, the wedge-like shape can be used as a feedback mechanism.

In some examples, the medial edge height 702 or the lateral edge height 704 can provide between 10 mm and 20 mm, inclusive, of spacing adjustment between a bearing component 342 (FIG. 4A) and a bearing support component, such as a base component 344 (FIG. 4A) or a plate component 350 (FIG. 4A). In some examples, the medial edge height 702 or the lateral edge height 704 can provide between 10 mm and 14 mm, inclusive, of spacing adjustment and an additional 0 mm to 6 mm of spacing adjustment can be provided by different sizes of the bearing support component.

FIGS. 9 and 10 illustrate side views of at least two versions of a shim component of a tibial prosthesis system. The shim component 346C of FIG. 9 includes an anterior edge height 706 that is the same or substantially the same as a posterior edge height 708. In contrast, the shim component 346D of FIG. 10 includes an anterior edge height 706 that is different than a posterior edge height 708. In the example shown, the anterior edge height 706 is less than the posterior edge height 708 and can be used by a surgeon to analyze possible bone cuts for a patient experiencing an anterior to posterior sloped knee joint. Alternatively, the anterior edge height 706 can be greater than the posterior edge height 708 and can be used by a surgeon to analyze possible bone cuts for a patient experiencing a poster to anterior sloped knee joint. Due to a height difference between the anterior and posterior edges, an inferior surface 461 of the shim component can include an anterior to posterior angle of between +3 degrees and −3 degrees, inclusive. The wedge-like shape of the shim component 346D can be used by the surgeon to assess kinematics of a knee joint if a particular bone cut is made. In this way, the wedge-like shape can be used as a feedback mechanism.

In some examples, the anterior edge height 706 or the posterior edge height 708 can provide between 10 mm and 20 mm, inclusive, of spacing adjustment between a bearing component 342 (FIG. 4A) and a bearing support component, such as a base component 344 (FIG. 4A) or a plate component 350 (FIG. 4A). In some examples, the anterior edge height 706 or the posterior edge height 708 can provide between 10 mm and 14 mm, inclusive, of spacing adjustment and an additional 0 mm to 6 mm of spacing adjustment can be provided by different sizes of the bearing support component.

In some examples, the shim components 346C and 346D can include an entry ramp 709, which can be similar to the entry ramp 614 described above and shown in FIG. 6B. A ratio R from a start of the ramp 709 to a beginning of a dovetail of each of the shim components 346C and 346D can be used to maintain engagement of the dovetails during a shim insertion procedure.

Figure 11:
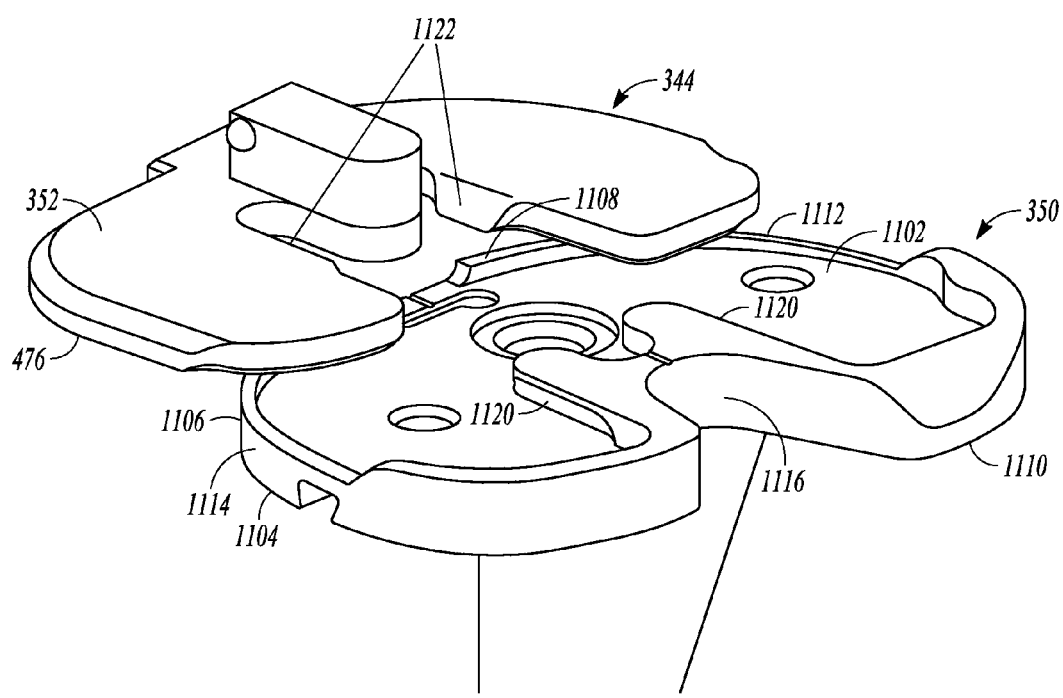
FIGS. 11-12B illustrate exploded views of a base component and a plate component of a tibial prosthesis system, as constructed in accordance with at least one embodiment.
Figure 12A:
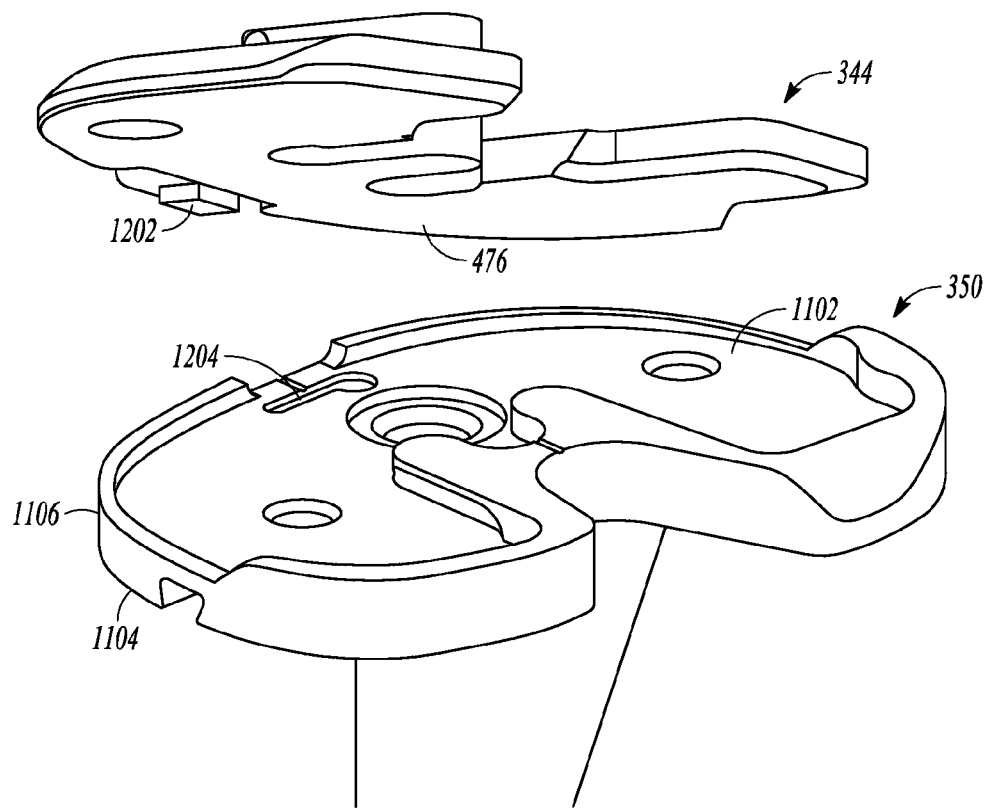
Figure 12B:
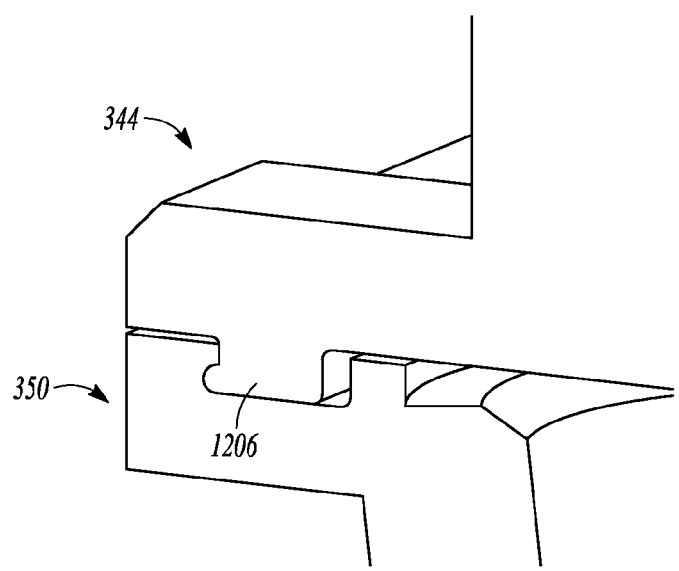

FIGS. 11, 12A, and 12B illustrate exploded views of a base component 344 and a plate component 350 of a tibial prosthesis system 340 (FIG. 4A). The plate component 350 can correspond closely in size and shape with a resected proximal tibial surface. The plate component 350 can include a superior surface 1102, an opposing bone contacting surface 1104, and a peripheral wall 1106 extending from the bone contacting surface 1104 to the superior surface 1102. The peripheral wall 1106 can include a raised perimeter, an anterior side 1108, a posterior side 1110, a medial side 1112, and a lateral side 1114. The plate component 350 can include a PCL cut-out 1116 disposed at the posterior side 1110 to accommodate a posterior cruciate retaining ligament of a knee joint. While the plate component 350 is part of the provisional prosthesis system disclosed herein, it can also be part of a permanent prosthesis system or a sizing system.

The base component 344 can be secured to the plate component 350 by positioning an inferior surface 476 of the base component 344 on the superior surface 1102 of the plate component 350. The base component 344 can include at least one ramped surface 1122 extending between its inferior surface 476 and its superior surface 352. The at least one ramped surface 1122 can be configured to engage one or more undercuts 1120 of the plate component 350. A dovetail-like engagement, for example, between the at least one ramped surface 1122 and the one or more undercuts 1120 can act to inhibit medial/lateral movement between the base 344 and plate 350 components. A perimeter undercut surrounding the inferior surface 476 of the base component 344 can further mate with the raised perimeter of the plate component 350 to inhibit anterior/posterior and medial/lateral movement between the base 344 and plate 350 components. To inhibit proximal/distal movement between the base 344 and plate 350 components, a locking projection 1202 can extend from the inferior surface 476 of the base component 344 and can be configured to engage with a locking cavity 1204 extending inferiorly from the superior surface 1102 of the plate component 350. As shown in FIG. 12B, the locking projection 1202 and the locking cavity 1204 can form an interference locking arrangement 1206.

Figure 13:
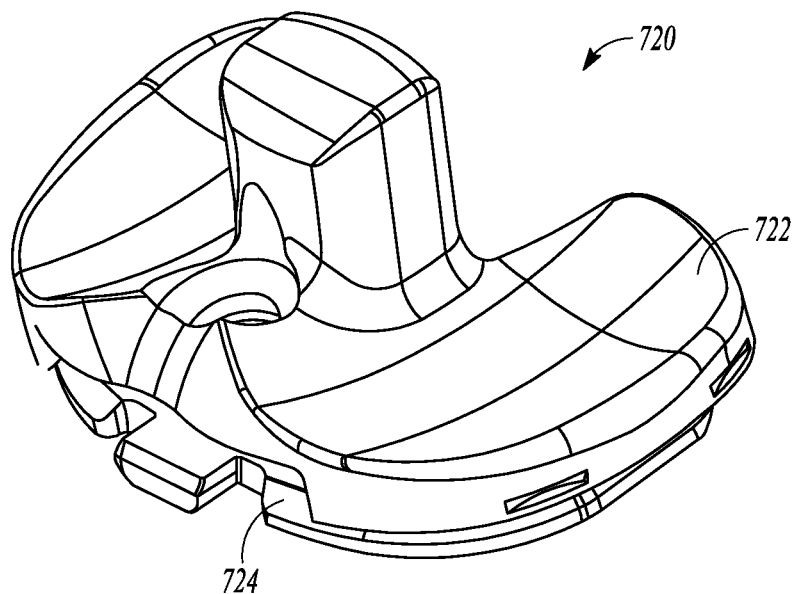
FIGS. 13-14 illustrate perspective views of portions of a tibial prosthesis system, as constructed in accordance with at least one embodiment.
Figure 14:
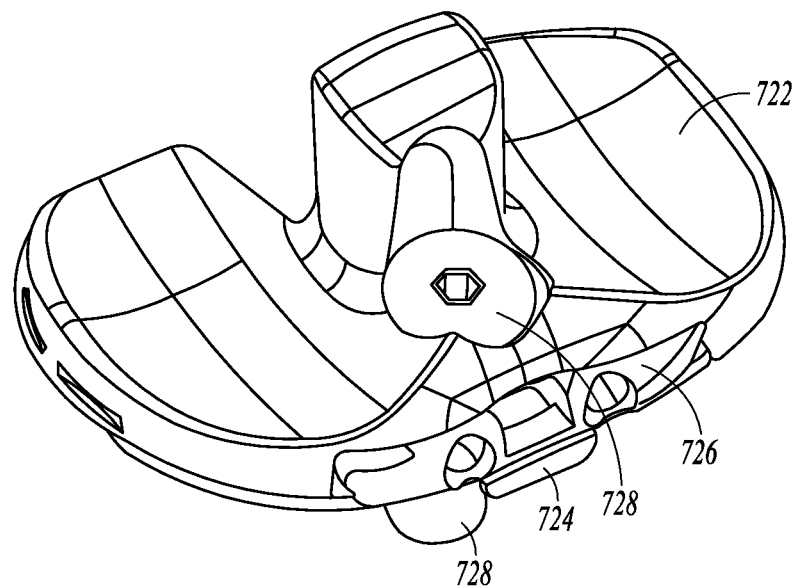

FIGS. 13 and 14 illustrate perspective views of portions of a tibial prosthesis system 720, which can be similar to portions of the tibial prosthesis system 340, described above, and used in preparation for selecting a permanent tibial prosthesis system. FIG. 13 shows a bearing component 722 and a base component 724. The base component 724 is also referred to herein as a bearing support component. FIG. 14 shows the bearing component 722 and the base component 724, similar to FIG. 13, as well as a spacer component 726 and a fastener 728. In an example, the tibial prosthesis system 720 can be used to mimic a total knee replacement procedure in which a surgeon decides that a posterior-stabilized (PS) implant is suitable for a particular patient. One or more portions of the tibial prosthesis system 720 can be used with a permanent tibial prosthesis system such as, for example, a PS implant. The fastener 728 can be used to "lock down" or secure the bearing component 722 to the base component 724. In an example, the fastener 728 can be a lockdown screw.

Figure 15A:
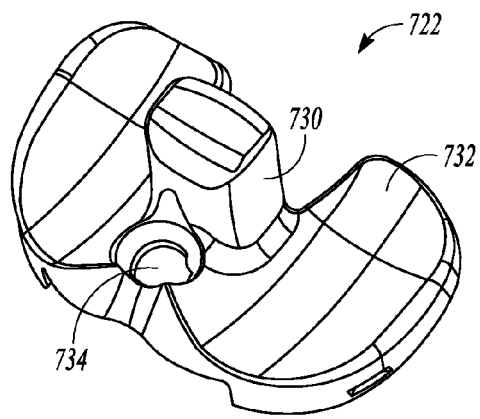
FIGS. 15A-15D illustrate various perspective views of a bearing component, as constructed in accordance with at least one embodiment.
Figure 15B:
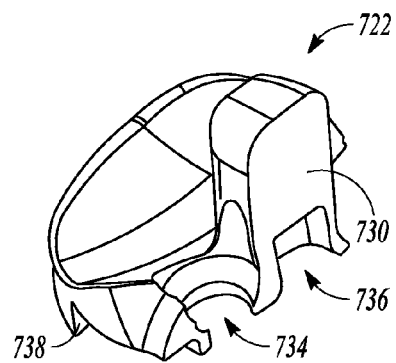
Figure 15C:
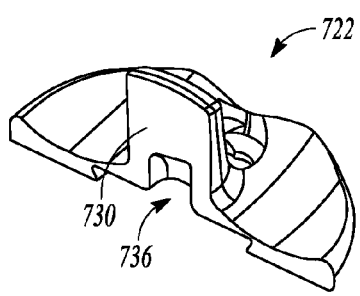
Figure 15D:
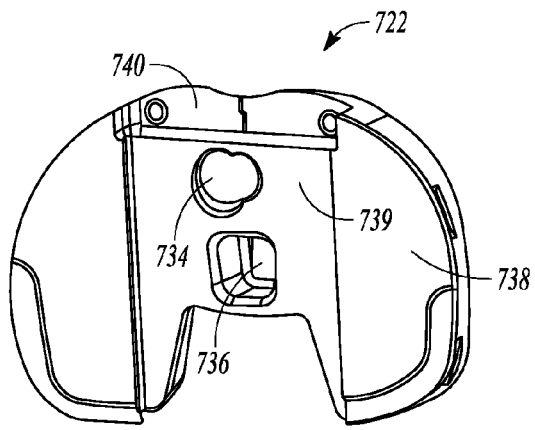

FIGS. 15A through 15D illustrate various perspective views of the bearing component 722 of FIGS. 13 and 14. FIG. 15A shows a superior or articulating side of the bearing component 722. FIG. 15B shows a portion of the bearing component 722 cut along a midline in an anterior/posterior direction. FIG. 15C shows a portion of the bearing component 722 cut along a midline in a medial/lateral direction. FIG. 15D shows an inferior or underside of the bearing component 722.

The bearing component 722 can include a post 730 extending from an articulating surface 732 and configured to engage with a femoral component, and an aperture 734 configured to receive the fastener 728 (see FIG. 14). The post 730 can include a pocket 736 extending from an inferior side 738 of the bearing component 722. The pocket 736 can have one or more planar walls in its cross-section geometry (e.g., trapezoidal cross-section geometry) to prevent or eliminate relative displacement between the bearing component 722 and the base component 724.

The inferior side 738 of the bearing component 722 can also include an opening 740 and a bottom portion 739 to receive one or both of the spacer component 726 (see FIG. 14) or a shim component, such as the shim component described below and illustrated in FIGS. 17-20.

Figure 16A:
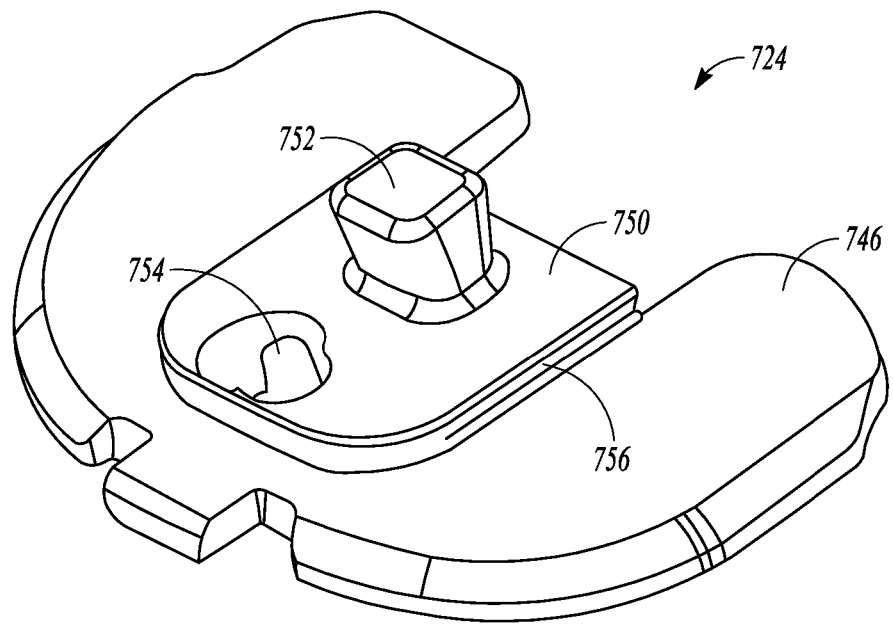
FIGS. 16A-16B illustrate superior and inferior sides, respectively, of a base component, as constructed in accordance with at least one embodiment.
Figure 16B:
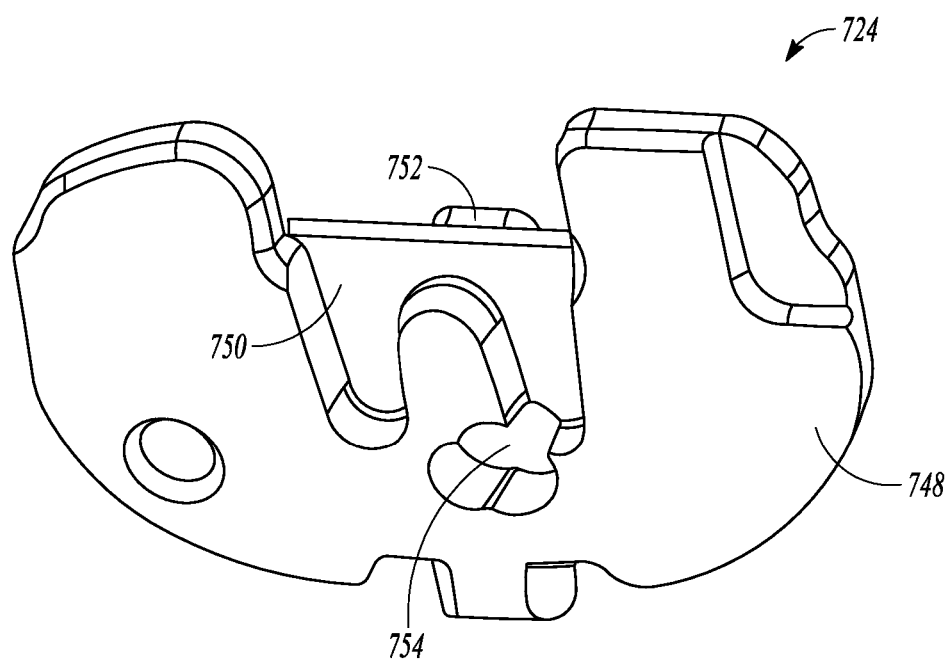

FIG. 16A illustrates a superior side 746 of the base component 724 and FIG. 16B illustrates an inferior side 748 of the base component 724. The base component 724 can include a platform 750 between medial and lateral component portions. The platform 750 can include a post 752 configured to align with the pocket 736 of the bearing component 722, and an aperture 754 configured to align with the aperture 734 of the bearing component 722 and receive the fastener 728.

The base component 724 can be configured such that a plane of symmetry for the post 752 is aligned with an axis of the opening 754. The position of the post 752 can help prevent an incorrect combination of a particular bearing component 722 and a particular base component 724. If a particular bearing component 722 and a particular base component 724 are not intended to be used together, relative positions of the bearing component and the base component features can be offset and insertion of a shim component can be prevented. This prevention can provide an indication of incompatibility. The base component 724 can include a rail 756 extending around the platform 750 and configured to engage with a shim component.

Figure 17:
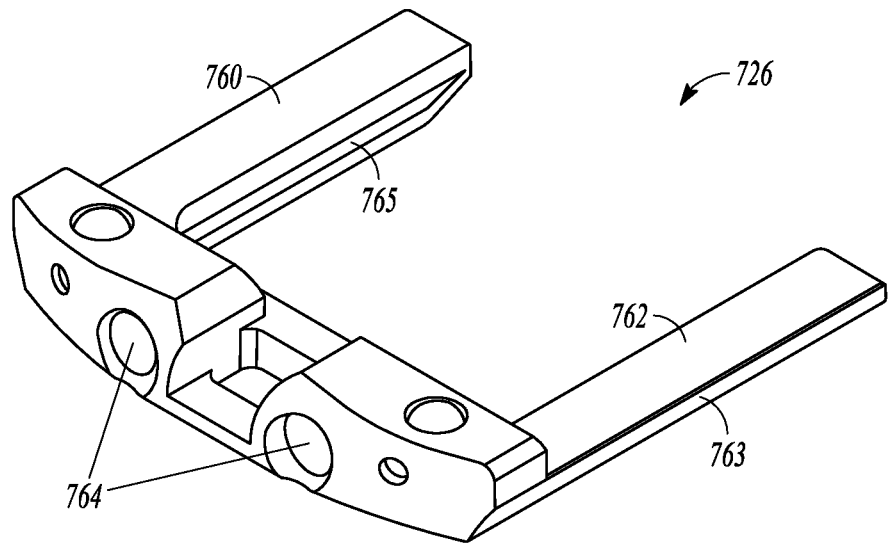
FIG. 17 illustrates a perspective view of a spacer component, as constructed in accordance with at least one embodiment.
Figure 18:
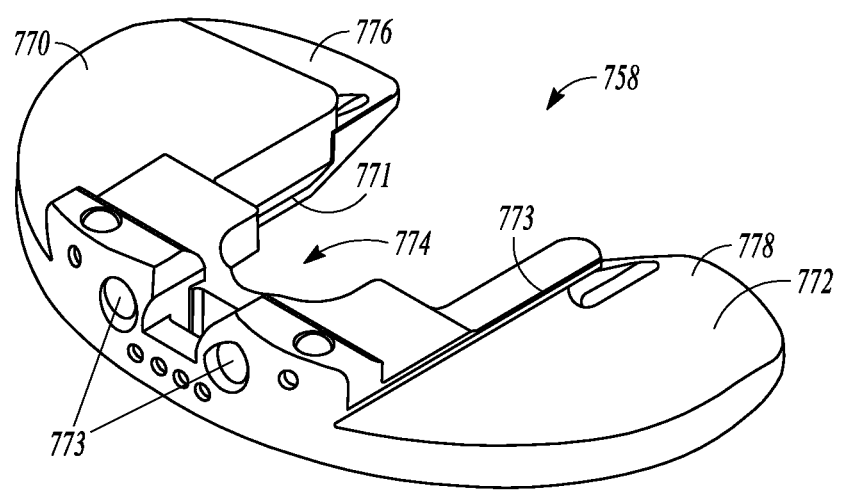
FIG. 18 illustrates a perspective view of a shim component, as constructed in accordance with at least one embodiment.

FIG. 17 illustrates a perspective view of the spacer component 726, which is illustrated in FIG. 14. FIG. 18 illustrates a perspective view of a shim component 758. In an example, the spacer component 726 can be available in a thinner size relative to the shim component 758. The spacer 726 and the shim component 758 can provide a similar function of providing spacing between the bearing component 722 and the base component 724, as similarly described above for shim component 346 (see FIGS. 4A and 4B). In an example, the spacer component 726 can provide a substantially similar spacing to a spacing provided between the bearing component 722 and the base component 724 when the two components 722 and 724 are assembled. The shim component 758 can be used in combination with or in lieu of the spacer component 726 to provide additional or tailored (e.g., differing medial/lateral or anterior/posterior) spacing, as described above and further described below. In an example, the spacer component 726 can be part of the tibial prosthesis system 720 as it is implanted in a knee joint. If additional or tailored spacing is needed between the bearing component 722 and the base component 724, the spacer component 726 can optionally be removed and the shim component 758 can be inserted.

As shown in FIG. 14, the spacer component 726 can be slidably inserted between the bearing component 722 and the base component 724. The spacer component 726 can include two extensions 760 and 762 configured to extend in an anterior/posterior direction when the spacer component 726 is inserted between the bearing component 722 and the base component 744. The extensions 760 and 762 can each engage with the inferior side 738 of the bearing component and the superior side 746 of the base component. Engagement between the extensions 760 and 762 and one or both of the bearing component 722 and the base component 724 can include a dovetail-like engagement. In an example, the extension 762 can include dovetail geometry 763 on an outer portion of the extension 762, which can be used to engage with dovetail geometry on the bearing component 722. In an example, engagement between the extensions 760 and 762 and the base component 724 can include rail geometry 765, which can match and mate with the rail 756 on the base component 724. The spacer component 726 can include one or more handling alignment voids 764, or other coupling structures, to engage with an interface of a handling instrument, such as the handling instrument 354 (FIG. 6A).

The shim component 758 of FIG. 18 can similarly be slidably inserted between the bearing component 722 and the base component 724 and can include a first paddle 770, a second paddle 772, one or more handling voids 773, as well as a cutout feature 774 between the first 770 and second 772 paddles. The cutout feature 774 can be configured to accommodate the lockdown screw 728. Similar to the extensions 760 and 762 of the spacer component 726, portions of the shim component 758 can engage with one or both of the bearing component 722 and the base component 744 can include a dovetail-like manner. In an example, the shim component 758 can include dovetail geometry 771, on a top surface, that mate with the bearing component 722 and rail geometry 773 that mate with the base component 724, on a bottom surface. In an example, one or both of the first 770 and second 772 paddles can include an entry ramp 776 and 778, respectively, on a top surface of the shim component 758. The entry ramps 776 and 778 can be similar to the entry ramp 709 shown in FIGS. 9 and 10.

The tibial prosthesis system 720 can be configured such that the spacer component 726 and the shim component 758 can both accommodate the lockdown screw 728 shown in FIG. 14. The lockdown screw 728 (FIG. 14) can be available in different sizes and a size of the screw can be selected based, in part, on a spacing between the bearing component 722 and the base component 724. For example, if there is significant spacing between the bearing component 722 and the base component 724, a longer screw can be used as compared to if there is less spacing between the bearing component and the base component 724.

The shim component 758 of FIG. 18 can be available in a plurality of sizes. As described above in reference to the shim component 346, a set of different sized shim components 758 can be provided in a kit to allow for varying levels of adjustment for the provisional tibial prosthesis system 720. Moreover, the shim component 758 of FIG. 18 can be modified to have a height difference between the anterior and posterior edges and/or the medial and lateral edges, as shown in FIGS. 8 and 10 in reference to the shim components 346B and 346D. Shim components having a height difference between the anterior and posterior edges and/or the medial and lateral edges can be included in the kit of different-sized shim components, which can also include different-sized shim components having a uniform height.

The spacer component 726 and the shim component 768 can be used in both left and right tibial prosthesis systems and need not be side-specific.

Figure 19:
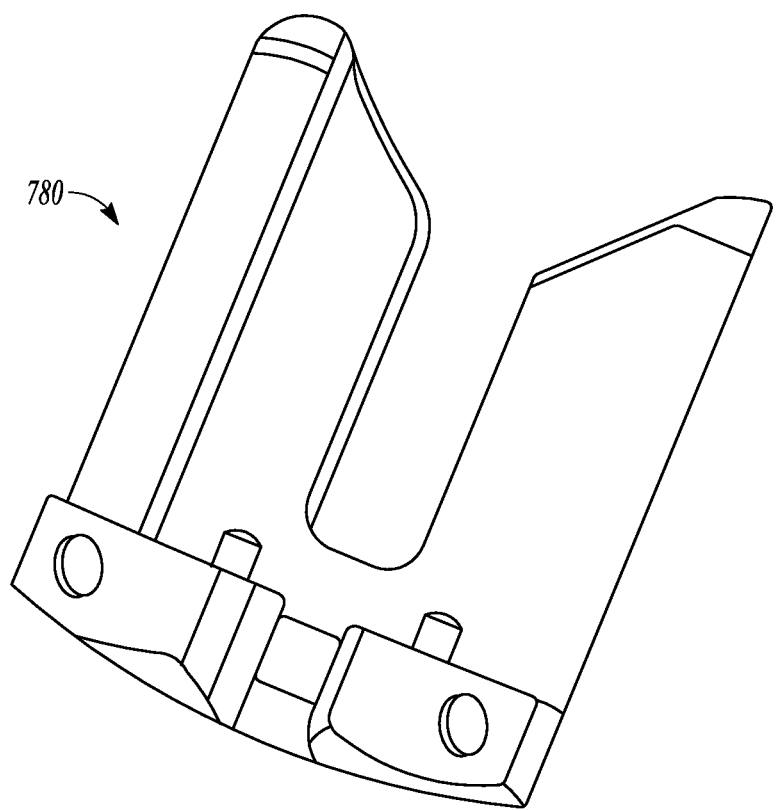
FIGS. 19-20 illustrate perspective views of a spacer component, as constructed in accordance with at least one embodiment.

FIG. 19 illustrates another example of a spacer component 780 that can be used in combination with a tibial prosthesis system. The spacer component 780 can be used with the tibial prosthesis system 340 shown in FIG. 4B. In an example, the spacer component 780 can be used to provide less spacing compared to the shim component 346. Similar to the spacer component 726, the spacer component 780 can be used, in some examples, to provide approximately the same spacing provided between the base component 344 and the bearing component 342. As similarly described above in reference to the spacer component 726, the spacer component 780 can be part of the tibial prosthesis system 340 when it is implanted in the knee. Although not visible due to its orientation in FIG. 19, the spacer component 780 can include one or more handling alignment voids for engaging with a handling instrument.

Figure 20:
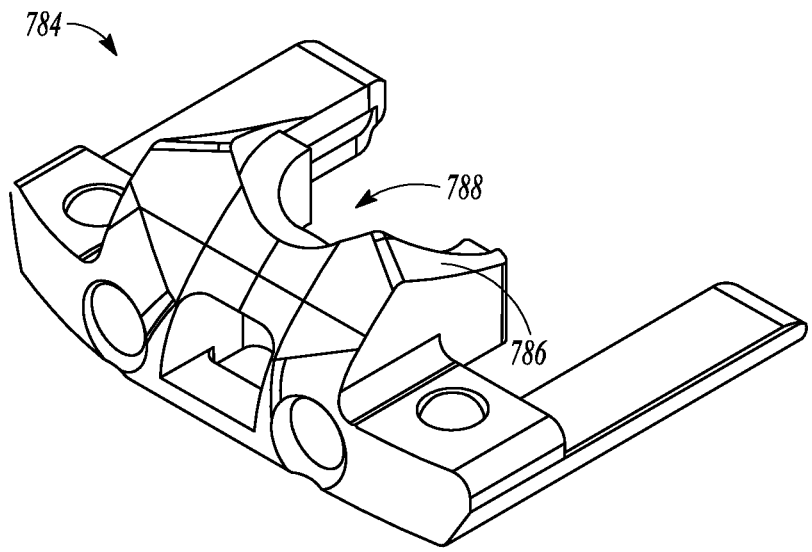

FIG. 20 illustrates an example of a spacer component 784 that can be similar to the spacer component 726 of FIG. 17 and can also include an extension 786. A cutout feature 788 can be formed in the extension 786 for accommodating a lockdown screw.

Figure 21:
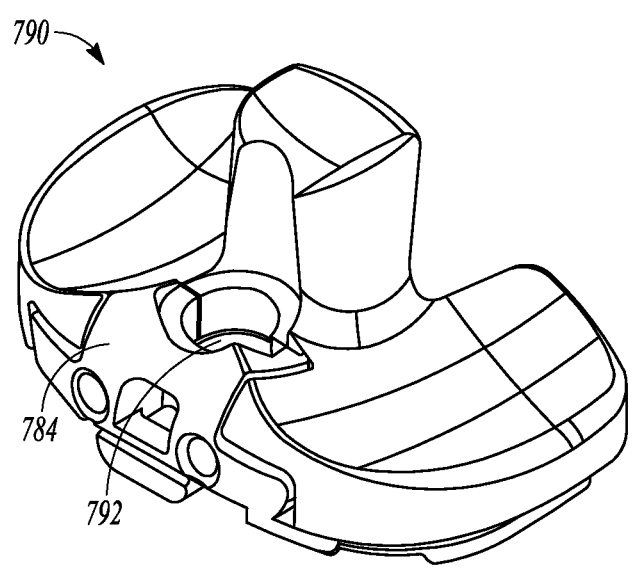
FIG. 21 illustrates a perspective view of a spacer component positioned in a tibial prosthesis system, as constructed in accordance with at least one embodiment.

FIG. 21 illustrates the spacer component 784 in a tibial prosthesis system 790, which can be similar to the tibial prosthesis system 720. The spacer component 784 can include the extension 786 and, together with an anterior portion of a bearing component, can form a portion of an aperture 792 configured to receive the fastener 728. In an example, the tibial prosthesis system 790 can be used for smaller size prostheses. As an overall size of the tibial prosthesis gets smaller, less material is available for clamping. The extension 786 can be used to provide additional material for clamping when a lockdown screw in inserted through the tibial prosthesis system 790 and into the aperture 792.

As described above in the method 500 of FIG. 5, after a provisional tibial prosthesis has been implanted in a tibia of a patient, testing can be performed to determine if proper knee joint kinematics are present. FIGS. 22-34 illustrate an example of a system for determining force balance on a knee joint during a surgical procedure, and the system can include full- or substantially full-surface sensing to determine knee joint kinematics, including soft tissue balance of the knee joint. The system can include, among other things, a user interface for displaying the sensed data as a two- or three-dimensional representation of an area or volume of the prosthesis, such as an articulation surface area of a tibial prosthesis. The various components of the system can be provided as a kit, as described below in reference to FIG. 29.

Figure 22:
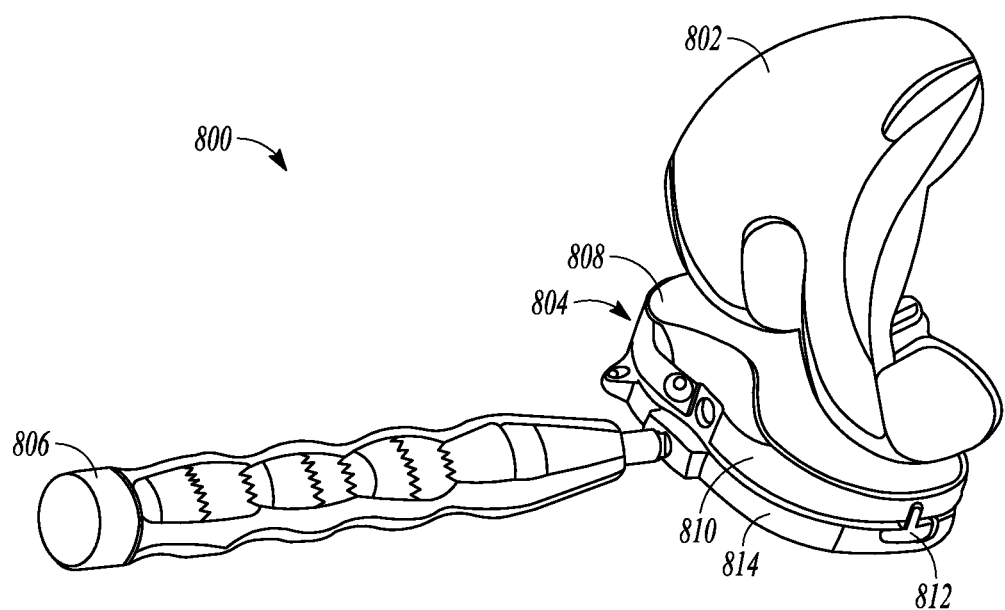
FIG. 22 illustrates a perspective view of a provisional or trial prosthesis system, as constructed in accordance with at least one embodiment.

FIG. 22 illustrates an example of a provisional or trial prosthesis system 800 for use in a knee surgery to provide full- or substantially full-surface sensing. The system 800 can be used in combination with a user interface for displaying sensing data. The trial prosthesis system 800 can include one or more of a provisional femoral prosthesis 802, a provisional tibial prosthesis system 804, and a handling instrument 806. The provisional tibial prosthesis system 804 can be similar to the provisional tibial prosthesis systems described above, and can include a bearing component 808, a shim component 810, a base component 812, and a plate component 814. The base component 812 and/or the plate component 814 are also referred to herein as a bearing support component.

Figure 23B:
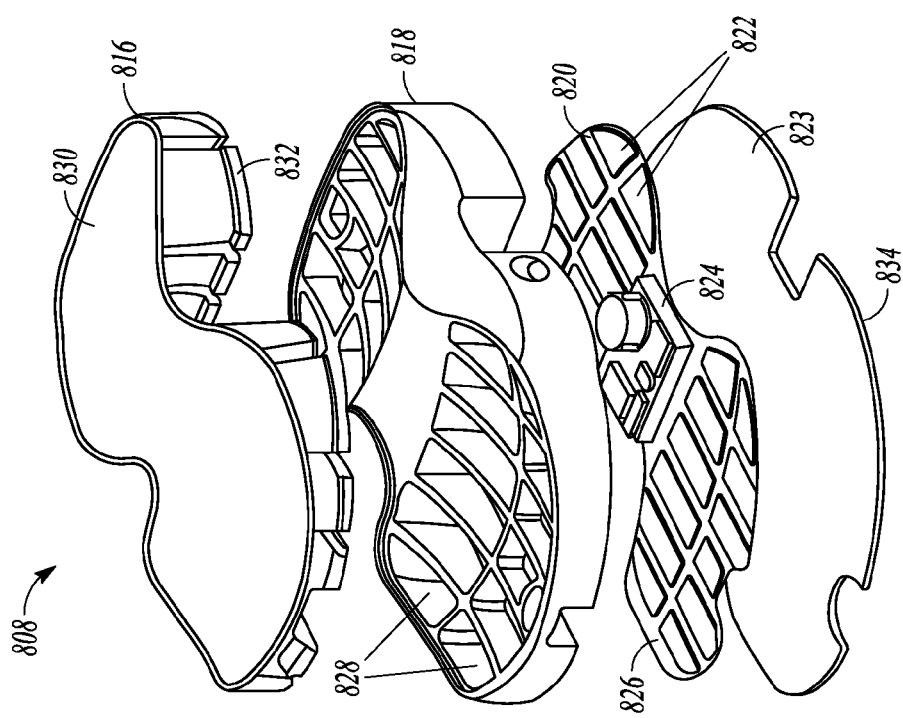
FIGS. 23A-23B illustrate assembled and component views, respectively, of a bearing component, as constructed in accordance with at least one embodiment.
Figure 23A:
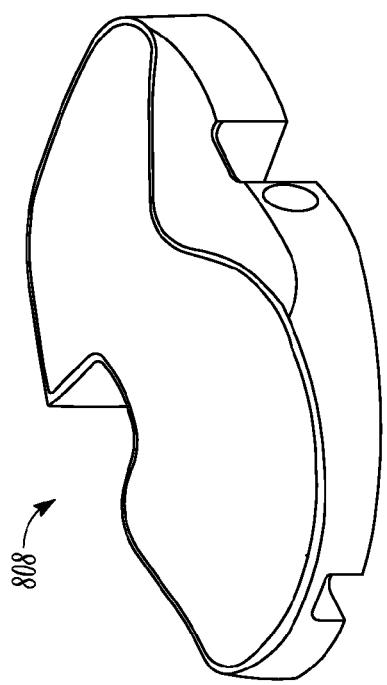

FIGS. 23A and 23B respectively illustrate assembled and component views of the bearing component 808. The bearing component 808 can be similar to the unitary bearing component 342 shown in FIG. 4B, or can include a plurality of components, such as a top portion 816, a frame 818, a sensor plate 820, and a bottom portion 823. The sensor plate 820 can include one or both of a plurality of sensors 822 or a processor 824, which can be disposed on a top surface 826 of the sensor plate 820. The frame 818 can include a plurality of apertures or openings 828 that can be sized and/or shaped to correspond to the plurality of sensors 822 on the sensor plate 820, thereby providing for precise force or pressure sensing. The top portion 816 of the bearing component 808 can include an articulating side 830 and a non-articulating side 832. The bottom portion 823 of the bearing component can be configured to support the sensor plate 820 and can form a bottom non-articulating side 834 of the bearing component 808.

Figure 24:
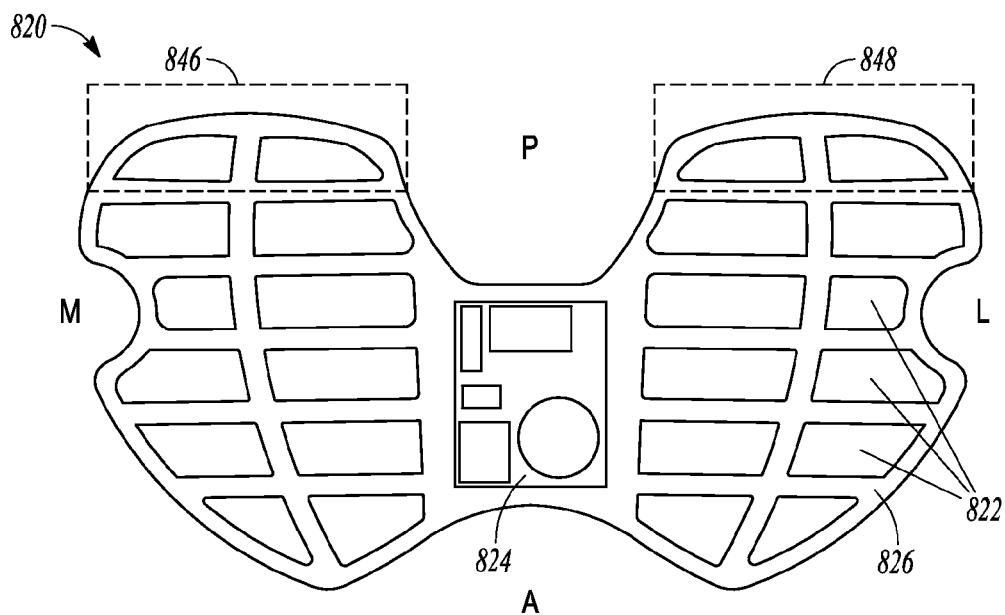
FIG. 24 illustrates a top surface of a bearing component sensor plate, as constructed in accordance with at least one embodiment.

FIG. 24 illustrates the top surface 826 of the sensor plate 820, including the sensors 822 and the processor 824. In an example, the sensor plate 820 can include twenty-four sensors 822. In other examples, a configuration and quantity of the sensors 822, as well as the frame 818, can be different than what is shown in FIG. 23B. The bearing component 808 can be configured such that there are multiple sensors 822 on the sensor plate 820 and the apertures 828 on the frame 818 can correspond to the sensors 822 in size, shape, or quantity.

The sensors 822 can include any suitable force or pressure sensors or readers, such as, but not limited to, piezoelectric sensors, force sensing resistors, force gauges, strain gauges, load cells, potentiometers, barometers, or the like. Example force sensors include force sensing resistor or capacitive flex circuits, piezoelectric film, piezoelectric elements, piezoresistive and piezoelectric polymers, metal foil strain gages, semiconductor strain gages, piezoresistive and capacitive pressure sensors, interferometric optical sensors, path displacement optical sensors, optical fiber force sensors, and other suitable sensing technologies.

The sensors 822 can occupy a substantial portion of the top surface 826 of the sensor plate 820 such that the sensors align with a substantial portion of the superior articulating surface of the bearing component 808, which can be an articulating side 830 of the top portion 816. The sensor plate 820 can have a medial side M, a lateral side L, an anterior side A, and a posterior side P, all of which can similarly apply to other components of the tibial prosthesis system 804. By configuring the sensors 822 to be generally spaced over a substantially portion of a surface that is parallel to, and aligned with, the articulating side 830 of the top portion 816, the sensors 822 can facilitate precise sensing on both the medial M and lateral L sides and/or anterior A and posterior P sides. Similarly, the sensors 822 can facilitate deep posterior sensing, as represented by a medial posterior region 846 and a lateral posterior region 848 in FIG. 24. Posterior sensing can be beneficial when determining high-flex balance and roll-back, and/or to predict wear, for example. Data gathered from the sensors 822 is described further below in reference to FIGS. 30-34.

Figure 25:
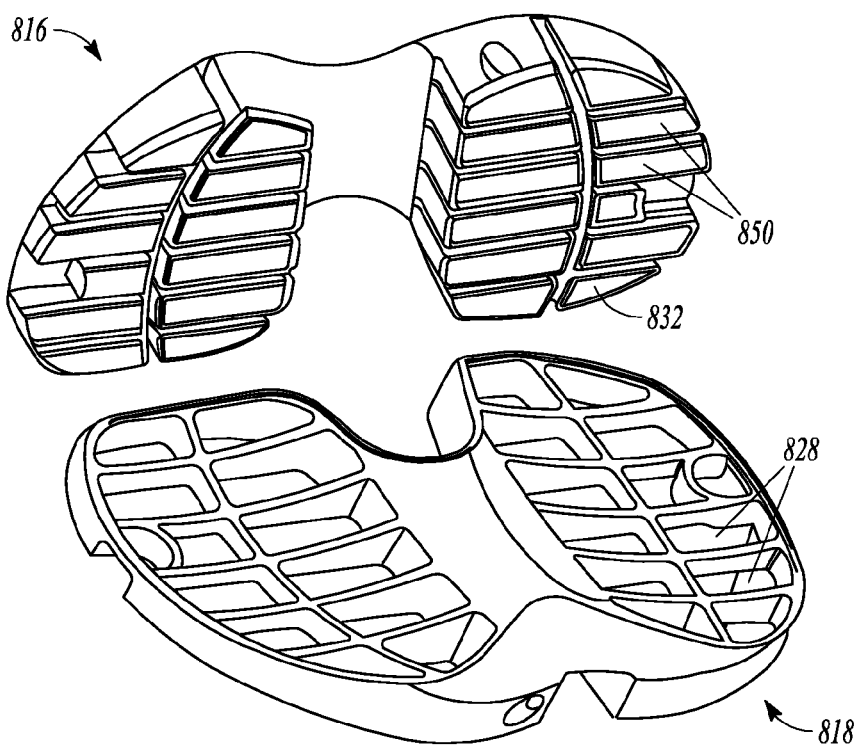
FIG. 25 illustrates a frame and a non-articulating side of a bearing component top portion, as constructed in accordance with at least one embodiment.

FIG. 25 illustrates the frame 818 and the non-articulating side 832 (or underside) of the top portion 816. The non-articulating side 832 of the top portion 816 can include a plurality of projections 850, each of which can be sized and shaped to fit within a corresponding aperture 828 on the frame 818. Alternatively, the plurality of projections 850 can be separate from, and positioned below, the top portion 816.

As described above, the apertures 828 on the frame can be configured to correspond and align with the sensors 822.

Thus, in response to a force on the articulating side 830 of the top portion 816, the projections 850 can be configured to transfer a representative force to one or more sensors 822 aligned with such force. The articulating side 830 of the top portion 816 can include inherent flexibility (e.g., via material properties or thickness) to allow applied forces to be appropriately measured by the aligned sensors 822 and processed for one or more knee joint balance determinations.

The isolated sensing compartments created by distinct projections 850 and distinct apertures 828 of the frame 818 can ensure that only forces applied directly above a particular one or more sensors 822 are measured. The projections 850 can be formed of the same or a different material than other portions of the top portion 816, and such material can be any material used in surgical procedures and having sufficient strength to sufficiently transfer force. In an example, the projections 850, or a portion thereof, can be formed of metal.

In an example, the top portion 816 can be formed through injection molding, and the projections 850 can be inserted into cavities of the top portion 816. The cavities of the top portion 816 can extend in a proximal-to-distal or distal-to-proximal direction and can correspond to a size and shape of the projections 850. Other designs can be used for the top portion 816 and the projections 850 in addition to what is shown in FIG. 25. By way of example, the articulating side 830 can be formed from a separate piece attachable to one or more other components used to form the top portion 816. In an example, the projections 850 can occupy a larger depth of the top portion 816, defined as a distance between the articulating side 830 and the non-articulating side 832. Once in place, the projections 850 can extend through a bottom of the top portion 816.

Figure 26A:
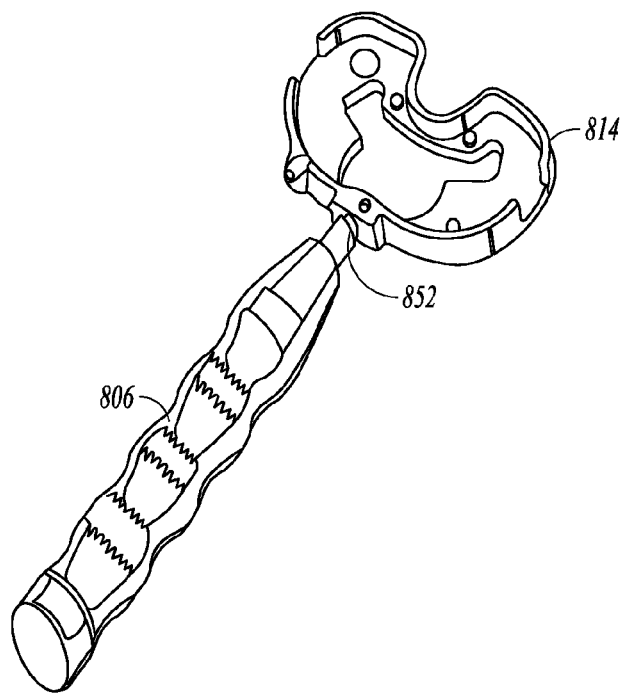
FIGS. 26A-27C illustrate one or more components of a provisional tibial prosthesis system in use with a handling instrument, as constructed in accordance with at least one embodiment.
Figure 26B:
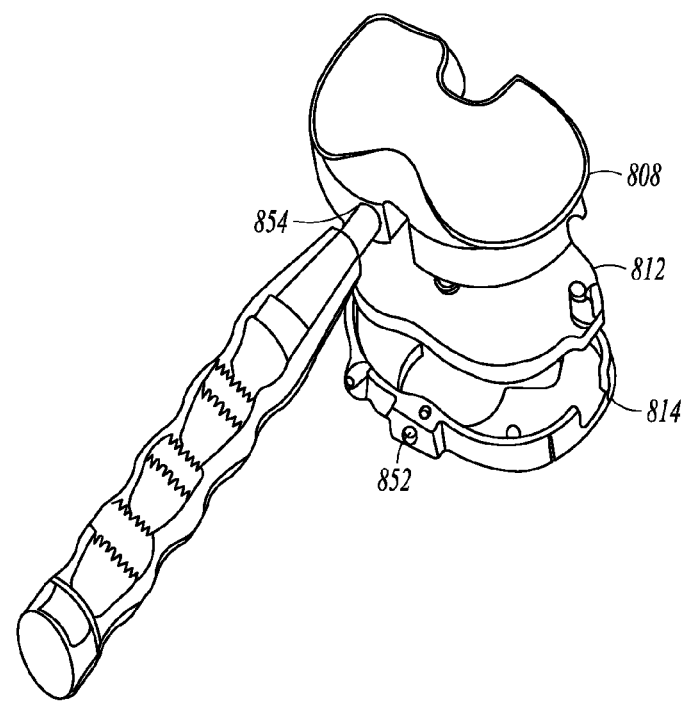

FIGS. 26A through 27C illustrate different components of the provisional tibial prosthesis system 804 in use with a handling instrument 806 shown in FIG. 22. This use can be similar to the shim handling instrument 354 shown in FIG. 6A and used with the provisional tibial prosthesis system 340. FIG. 26A shows the plate component 814 of the tibial prosthesis system 804 attached to the handling instrument 806. In an example, the plate component 814 can be attached to the handling instrument 806 using a handling alignment void 852 in an anterior portion of the plate component 814. FIG. 26B shows the bearing component 808 attached to the handling instrument 806 using a handling alignment void 854 formed in an anterior portion of the bearing component 808. The handling instrument 806 can be configured to releasably secure various components of the tibial prosthesis system 804, as further shown in FIG. 27A. In an example, the handling instrument 806 can be configured to engage with one handling void in the component it secures. In other examples, the handling instrument 806 can be configured to engage with two handling voids in the component it secures.

In an example, the bearing component 808, the base component 812, and the plate component 814 can be assembled together in preparation for implanting the tibial prosthesis system 804 on a tibia, and the handling instrument 806 can be attached to the plate component 814, as shown in FIG. 22. The shim component 810 can be included within the tibial prosthesis system 814, as shown in FIG. 22, when the other components are implanted, or the shim component 810 can be implanted in a later step.

Figure 27A:
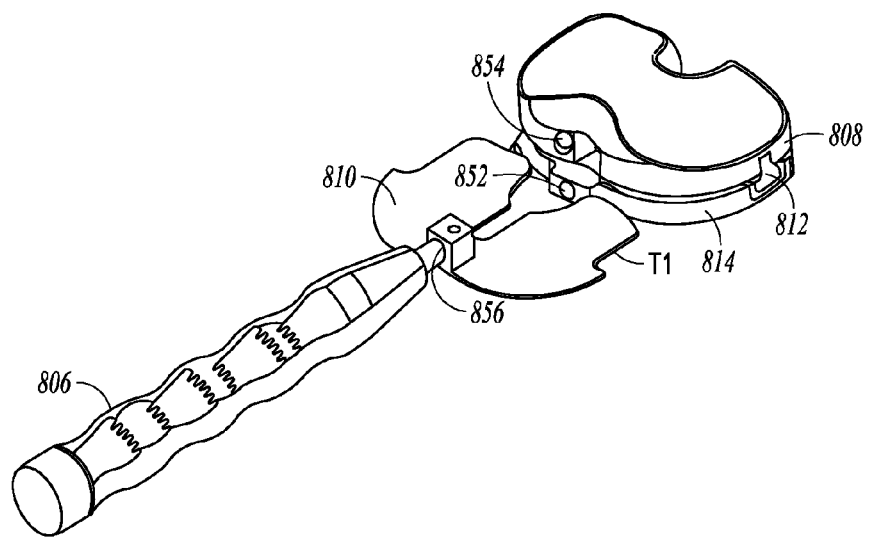
Figure 27B:
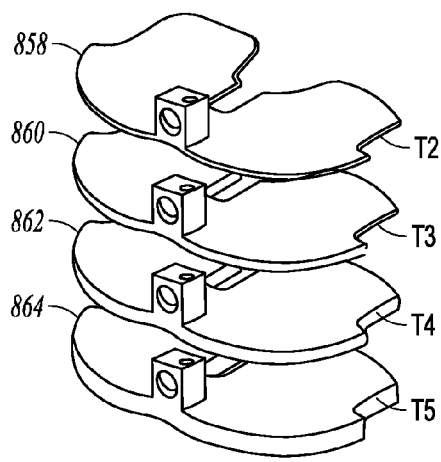

FIG. 27A illustrates the shim component 810 attached to the handling instrument 806 with a handling alignment void 856, and prior to inserting the shim component 810 between the bearing component 808 and the base component 812. In an example, the shim component 810 can have a thickness T1. FIG. 27B illustrates additional shim components 858, 860, 862 and 864 of increasing thicknesses (in a proximal to distal direction). A thickness T2 of the shim component 858 can be greater than the thickness T1 of the shim component 810. Similarly, a thickness T3 of the shim component 860 can be greater than the thickness T2 of the shim component 858. In an example, the shim components 810, 858, 860, 862 and 864 can have a thickness range between 10 mm and 14 mm, inclusive.

As described above in reference to the tibial prosthesis system 340, a particular shim component can be selected for insertion based on a distance between the bearing component 808 and the base component 812 implanted on a tibia. Also, as described above in reference to the method 500 of FIG. 5, a chosen shim component, selected from the shim components 810, 858, 860, 862 and 864, can be inserted and then testing can be performed to determine if a different shim component should be selected to replace an initially selected shim component. In an example, testing can be performed to analyze a force or pressure balance on at least a portion of the knee joint using the sensors 822 of the bearing component 808. If the force or pressure data collected is not satisfactory, a different shim component can be inserted. These steps can be repeated until satisfactory force or pressure data is observed. Optionally, in conjunction with or in lieu of shim selection, a surgeon can adjust ligament balance through ligament release if testing balance data is not satisfactory. The bearing component 808, which includes the sensors 822 and the frame 818, can be configured for providing a comprehensive set of sensing data about a force balance on a knee joint.

Figure 27C:
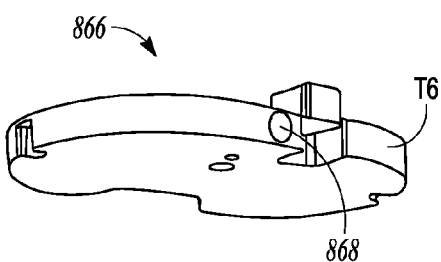

FIG. 27C illustrates a shim component 866 having a thickness T6. In an example, the thickness T6 of the shim component 866 can be less than the thickness T1 of the shim component 810. In an example, the thickness T6 of the shim component 866 can be about 6 mm. In other examples, the thickness T6 can be less than or greater than 6 mm. In an example, the shim component 866 can be used in combination with one of the shim components 810, 858, 860, 862 and 864 to provide additional spacing between the bearing component 808 and the base component 812. As shown in FIG. 27C, the shim component 866 can include an aperture 868 for engaging with the handling instrument 806 and can be configured for insertion between a shim component and the bearing component 808.

Figure 28:
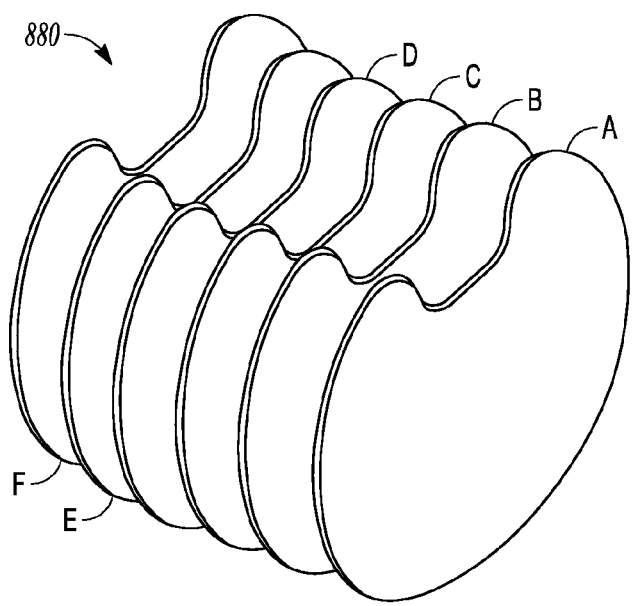
FIG. 28 illustrates a plurality of templates for determining a proper tibial tray size prior to selecting a tibial prosthesis system, as constructed in accordance with at least one embodiment.

The components of the trial prosthesis system 800 can be available in varying sizes to accommodate different size knee joints. In an example, a surgeon or other caregiver can determine an approximate suitable size or shape of the trial prosthesis system 800 using a template. FIG. 28 illustrates a plurality of templates 880 that can be sized and/or shaped for use in determining a proper tibial tray size prior to selecting a suitable size or shape of the tibial prosthesis system 804. The templates 880 can range in size from a smallest size A to a largest size F, as shown.

Figure 29:
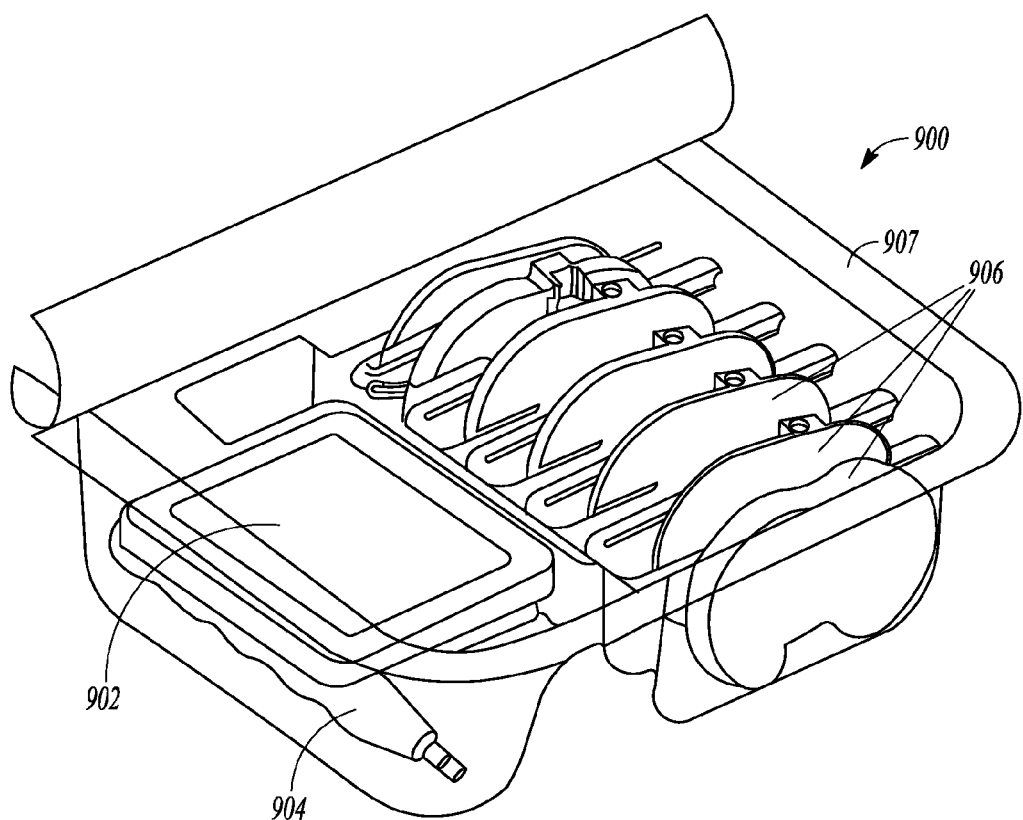
FIG. 29 illustrates an example of a kit that can include a user interface, a handling instrument, and a plurality of components of a trial prosthesis system, as constructed in accordance with at least one embodiment.

FIG. 29 illustrates an example of a kit 900 that can include a user interface 902, a handling instrument 904, and a plurality of components 906 that can include some or all of the components described above for the trial prosthesis system 800, or related variants of such components also described above. The user interface can be configured to be connected to the sensors 822 and the processor 824 of the bearing component 808 of the tibial prosthesis system 804. The user interface 902 can include a computing device configured to process data from the sensors 822 or the processor 824, compare such data to a historical database, and display one or more balance determinations on a screen of the user interface. The user interface 902 can be configured to be small and portable, as well as wireless, such that the user interface 902 can be used in an area, or surrounding area, of a surgical procedure. In some examples, the user interface 902 can be connected to another display device such as, for example, a computer or TV monitor in the area of the surgical procedure.

In an example, the kit 900 can include all components for the trial prosthesis system 800, including the provisional femoral prosthesis 802 and a plurality of shim components, as described above in reference to FIG. 27B. In an example, the kit 900 can include at least one shim component having a height difference between the anterior and posterior edges and/or the medial and lateral edges. The kit 900 can be designed such that the user can have some or all of the components for the knee procedure located together. The components of the kit 900 can be housed inside a tray 907 that, together with one or more of the components that it houses, can be disposable after a single use. In an example, the kit 900 can include some of the components of the trial prosthesis system 800 and some of the other components can be provided separately during the surgical procedure.

Figure 30:
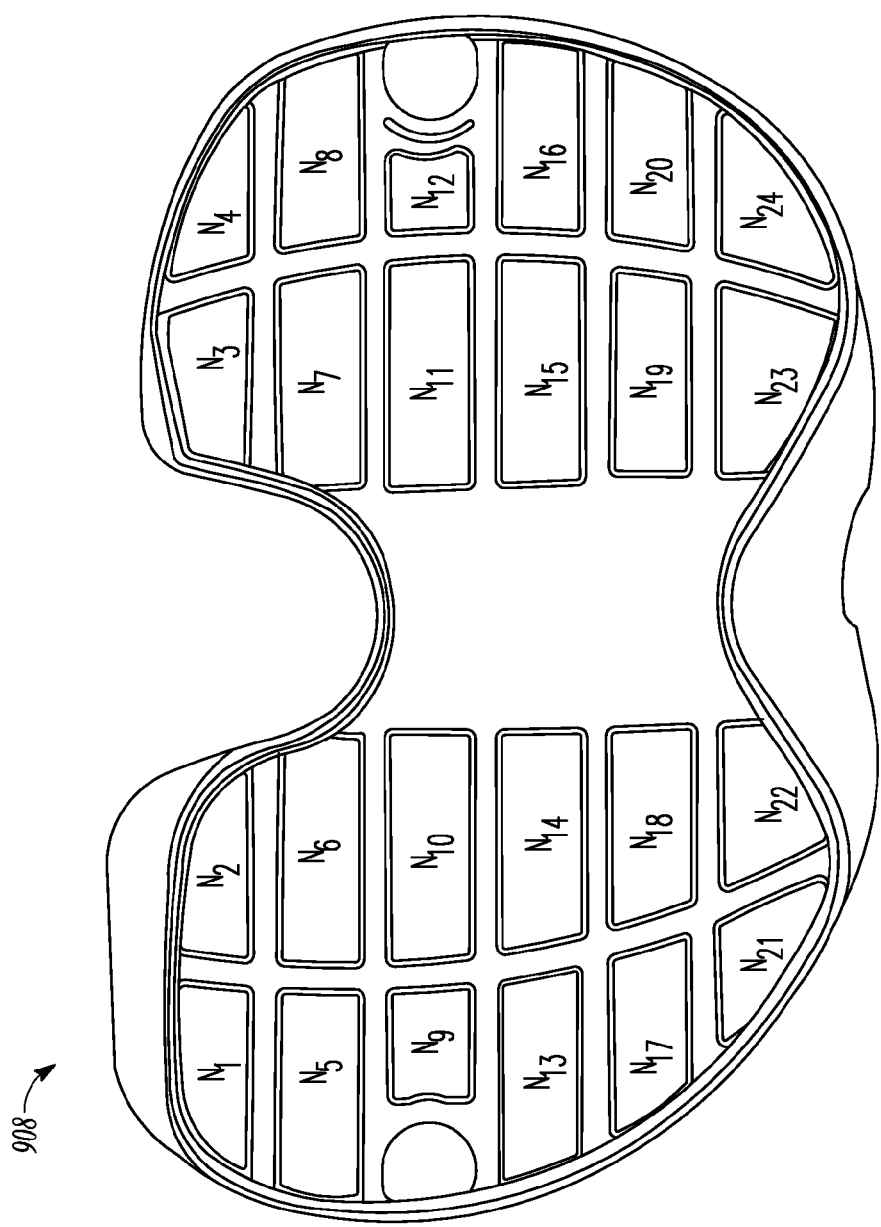
FIGS. 30-34 illustrate digital images that can be generated and displayed on a user interface, as constructed in accordance with at least one embodiment.

FIG. 30 illustrates an example of a digital image 908 that can be generated and displayed on the user interface 902. As described above, the bearing component 808 of the tibial prosthesis system 804 can include the sensor plate 820 having the plurality of sensors 822. In an example, the sensor plate 820 can have a twenty-four sensor configuration. The sensor plate 820 can include the processor 824, which can be configured to receive and process data from the plurality of sensors 822 before communicating the data to the user interface 902. The processor 824 can alternatively be integrated with the computing device of the user interface 902. The user interface 902 can have a wired or wireless connection with the sensor plate 820. The wired or wireless connection can utilize any type of network, such as the Internet, a telephone network, a cable network, or a wireless network.

The digital image 908 can be a two-dimensional (shown), or optionally three-dimensional, representation of the area of the tibial prosthesis 800 that is aligned with the sensors 822. The data from the sensors 822 can be mapped into a multi-point data registry. In an example, a 24-point data registry is mapped based on having twenty-four sensors 822. In other examples, the data registry can have more or less than twenty-four points based on having more or less than twenty-four sensors 822 on the sensor plate 820. As described above, a configuration and design of the bearing component 808, including the frame 818 having the openings 828 aligned with the sensors 822, can allow for independent sensing areas that can be noticeably mapped and presented on the user interface 902.

Figure 31:
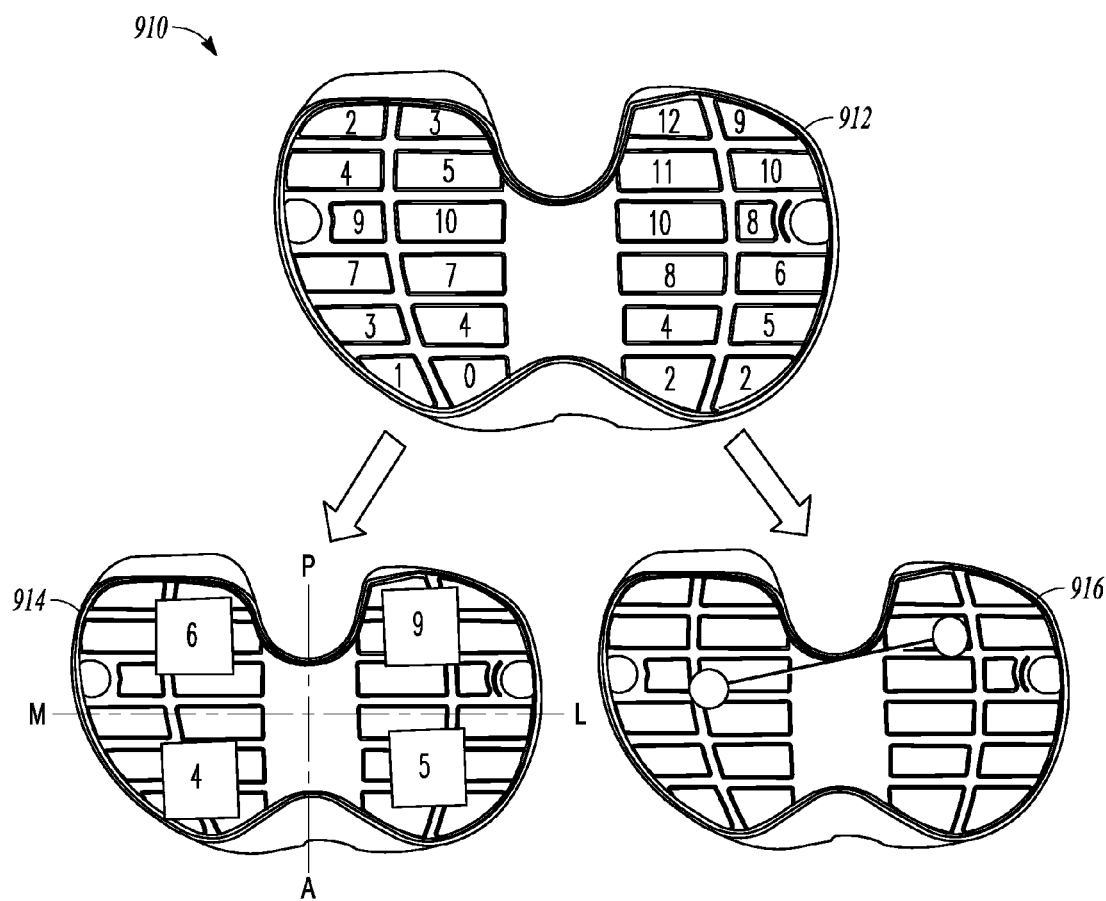

FIG. 31 illustrates an example of a digital image 910 that can be displayed on the user interface 902. The digital image 912 can show a force value generated by each of the sensors 822 on the sensor plate 820. The force value generated can be the result of force transmitted by the projections 850 of the top portion 816, or alternatively, columns extending between the top portion 816 and the bottom portion 823, which interact with the sensors 822. Based on the data shown in the digital image 912, the computing device of the user interface 902 can generate an image 914, which can include a collective force in each of two halves or four quadrants on the provisional tibial prosthesis system 804. The image 914 can include indicators representing medial M, lateral L, anterior A, and posterior P sides, or combinations thereof, of the provisional tibial prosthesis system. An image 916 showing medial-lateral and anterior-posterior center of force data can also be generated by the user interface 902.

Figure 32:
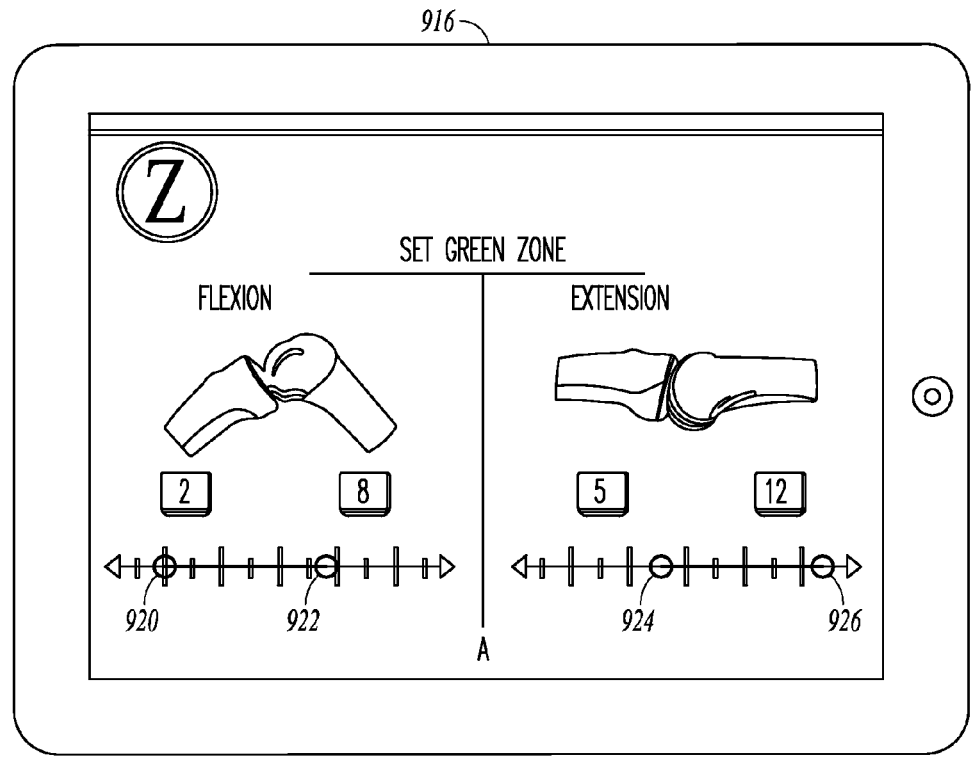

FIG. 32 illustrates an example of another digital image 918 that can be displayed on the user interface 902. The surgeon or other user can select a particular zone, which can be conceptualized as a green or safe zone, representing acceptable force limits in flexion and/or extension. In flexion, the green zone can be represented by limit points 920 and 922, for example, and in extension, the green zone can be represented by limit points 924 and 926, for example. Optionally, the green zone can be established based, at least in part, on statistically relevant historical data from one or more patient trials. For example, upon the collection of a number of trials of empirical data, data may be statistically analyzed (either by the analysis program, or another external program) to form suggested pre-determined pressure criteria, i.e., upper and lower limits, to aid the surgeon in recognizing potential elevated pressure readings. The suggested pre-determined pressure criteria can define statistically sound thresholds and allowable limits under certain conditions, and can be constantly adjusted as more information becomes available in the database.

Figure 33:
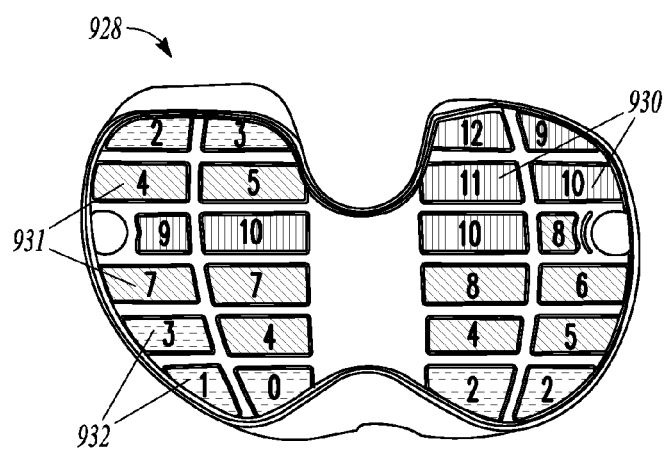
Figure 34:
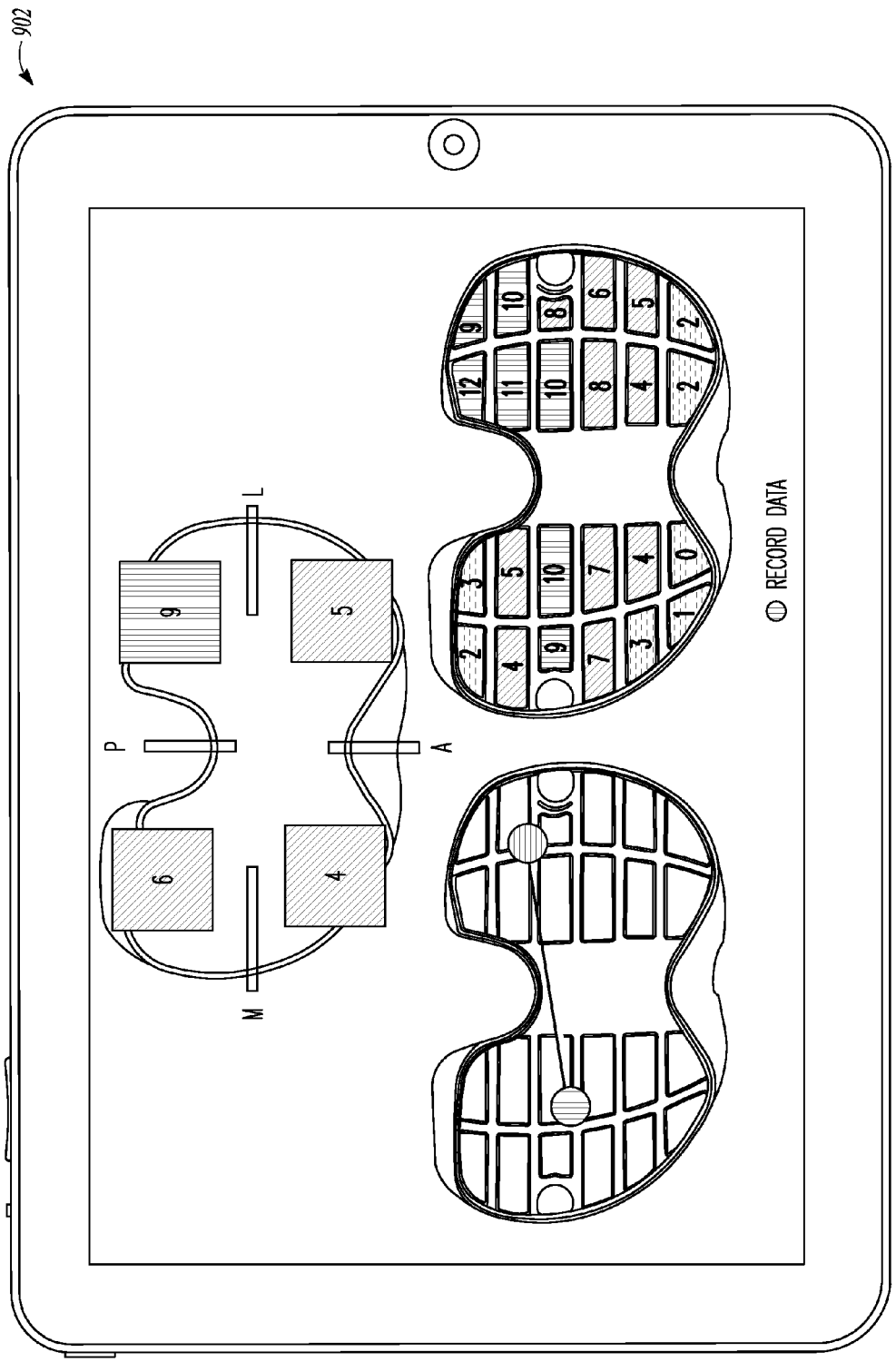

Forces values generated by, and acquired from, the sensors 822 can then be mapped and shown in image 928 of FIG. 33, for example. The image 928 can indicate forces or force zones (e.g., medial zone, lateral zone, anterior zone, posterior zone, medial/anterior zone, medial/posterior zone, lateral/anterior zone, or lateral/posterior zone) that are too high (labeled as 930) relative to the green zone, within the acceptable green zone (labeled as 931), and that are too low (labeled as 932) relative to the green zone. The computing device of the user interface can be configured to compare the acquired force data to green zone data, the latter of which can be stored in software on the user interface's hard drive. FIG. 34 illustrates the user interface 902 with multiple images based on the green zone selected by the surgeon. One or more images can be used by the surgeon, for example, to correct excessive forces or force zones.

In other examples, additional or alternative data can be displayed to guide the surgeon. The numbers presented as force values in FIGS. 31-34 are exemplary to show the type of data that can be generated and displayed for use by the surgeon. The particular numbers represented are not intended to be limiting, but rather, an example for determining balance or imbalance of the knee joint. The force numbers generated by the sensors and mapped into the data point registry can be compared to previously gathered numbers over time that can be indicative of adequate to inadequate balance and alignment.

In an example, as described above, the user interface 902 can be configured to include a computing device and the user interface 902 can be provided as part of the kit 900. In other examples, the sensors 822 and the processor 824 can be connected to any other type of computing device to generate the types of data described above, based on the data from the sensors 822.

Closing Notes:

Existing provisional systems, kits, and methods fail to provide a surgeon with insight of knee joint kinematics if an angled bone cut (e.g., a bone cut that is not parallel to a joint line of a knee) is made to a distal end of a femur or a proximal end of a tibia. Existing provisional systems, kits, and methods further require the stacking of a relatively high number of provisional components to arrive at an appropriate configuration of a permanent tibial prosthesis system or fail to provide sensed force or pressure data providing a real-time indication of provisional knee joint balance.

Advantageously, the present provisional systems, kits, and methods can include a shim component, having one or both of a medial edge height that is different than a lateral edge height or an anterior edge height that is different than a posterior edge height, or a sensor coupled to or integrated with a bearing component, a bearing support component, or the shim component. Such a shim component configuration can provide the surgeon with knee joint kinematic insight regarding an angled bone cut to the femur or tibia before the cut is made and can reduce the number of provisional components needed during surgery sizing. The sensor can facilitate real-time knee joint balancing testing.

The above Detailed Description includes references to the accompanying drawings, which form a part of the Detailed Description. The drawings show, by way of illustration, specific embodiments in which the present tibial prosthesis systems, kits, and methods can be practiced. These embodiments are also referred to herein as "examples." While certain examples are shown and described with respect to a left knee or a right knee, it is to be appreciated that the present disclosure is equally applicable to both the left and right knees. All examples can also be used in partial or total knee replacement procedures.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient. In this document, the phrase "anterior/posterior direction" is used to include an anterior to posterior direction or a posterior to anterior direction.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Also, in the following claims, the "kit" claims are intended to provide protection for, among other things, a set novel shim components, at least one of which includes differing heights, and sensor, bearing support, and handling instrument components having a functional relationship with the novel shim components. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A system for determining force balance on a knee joint during a surgical procedure, the system comprising:
a tibial prosthesis including a bearing component, a base component, and a shim component, the bearing component, having a superior articulating surface and an inferior surface, and comprising a top portion, a bottom portion, a frame disposed between the top portion and the bottom portion, a plurality of sensors disposed between a superior surface of the frame and the bottom portion, the frame having a plurality of apertures corresponding in a size or shape to the plurality of sensors, the base component having a superior surface and an inferior surface, the shim component configured to be slidable between the inferior surface of the bearing component and the superior surface of the base component, and a plurality of distinct projections extending from the top portion of the bearing component that are sized and shaped to fit within the plurality of apertures of the frame and positioned between the superior articulating surface and the inferior surface of the bearing component, each of the plurality of distinct projections is configured to operatively engage with at least one of the plurality of sensors.

2. The system of claim 1, wherein the plurality of sensors are positioned on a plate disposed between the frame and the bottom portion.

3. The system of claim 2, wherein the plurality of sensors occupies a substantial portion of the plate such that the sensors align with a substantial portion of the superior articulating surface of the bearing component.

4. The system of claim 1, wherein the plurality of sensors is selected from the group consisting of piezoelectric sensors, force sensing resistors, strain gauges, force gauges, load cells, potentiometers, barometers, other pressure sensors, and other force sensors.

5. The system of claim 1, further comprising a user interface providing a representation of an area or volume of the tibial prosthesis for presentation on a display, the representation comprising a medial/lateral indication and an anterior/posterior indication.

6. The system of claim 5, further comprising a wired or wireless connection between the plurality of sensors and the user interface.

7. The system of claim 5, wherein the user interface includes at least one force center indicator for presentation on the display and based on sensed force or pressure data and sensor locations from at least a first subset of the plurality of sensors, and the at least one force center indicator is indicative of balance or imbalance between force or pressure levels on the knee joint.

8. The system of claim 5, further comprising a processor, configured to receive and process information from the plurality of sensors, in communication with the user interface.

9. The system of claim 8, wherein the processor is included in the tibial prosthesis.

10. The system of claim 1, wherein the shim component is selected from a plurality of shims based on a proximal/distal spacing between the bearing component and the base component.

11. The system of claim 10, wherein the plurality of shims includes different-sized shims and at least one shim includes one or both of a medial edge having a different height than a lateral edge or an anterior edge having a different height than a posterior edge.

12. A system for determining force balance on a knee joint during a surgical procedure, the system comprising:
- a tibial prosthesis including a bearing component and a base component, the bearing component, having a superior articulating surface and an inferior urface, and comprising a top portion, a bottom portion, a frame disposed between the top portion and the bottom portion, a plurality of sensors disposed between a superior surface of the frame and the bottom portion, the frame having a plurality of apertures corresponding in a size or shape to the plurality of sensors, the base component having a superior surface and an inferior surface, and a plurality of distinct projections extending from the top portion of the bearing component that are sized and shaped to fit within the plurality of apertures of the frame and positioned between the superior articulating surface and the inferior surface of the bearing component, each of the plurality of distinct projections is configured to operatively engage with at least one of the plurality of sensors;
- at least one shim component configured to be slidable between the inferior surface of the bearing component and the superior surface of the base component in an anterior/posterior direction, the at least one shim component selected from a plurality of shim components of varying sizes;
- a user interface having a representation of an area or volume of the tibial prosthesis for presentation on a display; and
- a connection between the user interface and the plurality of sensors, configured such that the user interface receives information from the plurality of sensors and provides at least one force center indicator of balance or imbalance on the knee joint for presentation on the display.

13. The system of claim 12, wherein the plurality of shim components of varying sizes includes a plurality of shim components having one or both of a medial edge having a different height than a lateral edge or an anterior edge having a different height than a posterior edge.

14. The system of claim 12, wherein the at least one shim component includes a first shim and a second shim, each of which is slidable between the inferior surface of the bearing component and the superior surface of the base component after the tibial prosthesis is inserted in the knee joint.

15. The system of claim 12, wherein the user interface comprises a plurality of sensor icons for presentation on the display, the sensor icons having locations on the display corresponding to a relative location of the sensors within the bearing component.

16. The system of claim 12, wherein the connection between the user interface and the plurality of sensors includes a processor, configured to receive and process force or pressure data from the plurality of sensors, and a computing device, that receives the force or pressure data from the processor, and wherein the processor and the computer device communicate wirelessly.

* * * * *